(12) United States Patent
Davis et al.

(10) Patent No.: US 9,175,249 B2
(45) Date of Patent: *Nov. 3, 2015

(54) ETHYLENEOXIDE BUTYLENEOXIDE BLOCK COPOLYMER COMPOSITIONS

(75) Inventors: James W. Davis, Argyle, TX (US); Howard Allen Ketelson, Dallas, TX (US); David L. Meadows, Colleyville, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 1149 days.

This patent is subject to a terminal disclaimer.

(21) Appl. No.: 12/831,890

(22) Filed: Jul. 7, 2010

(65) Prior Publication Data

US 2011/0008276 A1 Jan. 13, 2011

Related U.S. Application Data

(60) Provisional application No. 61/223,599, filed on Jul. 7, 2009.

(51) Int. Cl.
| | |
|---|---|
| *A61K 31/765* | (2006.01) |
| *C11D 3/48* | (2006.01) |
| *A61K 9/00* | (2006.01) |
| *A61K 31/736* | (2006.01) |
| *A61K 31/77* | (2006.01) |
| *A61K 47/34* | (2006.01) |
| *A61K 47/36* | (2006.01) |
| *C11D 1/00* | (2006.01) |
| *C11D 3/22* | (2006.01) |

(52) U.S. Cl.
CPC ............ *C11D 3/48* (2013.01); *A61K 9/0048* (2013.01); *A61K 31/736* (2013.01); *A61K 31/77* (2013.01); *A61K 47/34* (2013.01); *A61K 47/36* (2013.01); *C11D 1/008* (2013.01); *C11D 3/222* (2013.01)

(58) Field of Classification Search
CPC .................................................. A61K 31/765
See application file for complete search history.

(56) References Cited

U.S. PATENT DOCUMENTS

| | | | |
|---|---|---|---|
| 2,174,761 A | 10/1939 | Schuette et al. | |
| 2,674,619 A | 4/1954 | Lundsted | |
| 2,828,345 A | 3/1958 | Spriggs | |
| 3,042,668 A | 7/1962 | Monti et al. | |
| 3,050,511 A | 8/1962 | Szware | |
| 3,829,506 A | 8/1974 | Schmolka et al. | |
| 4,057,598 A | 11/1977 | Lundberg et al. | |
| 4,104,824 A | 8/1978 | Lundberg et al. | |
| 4,130,517 A | 12/1978 | Lundberg et al. | |
| 4,136,173 A | 1/1979 | Pramoda et al. | |
| 4,218,327 A | 8/1980 | Wellington | |
| 4,360,451 A | 11/1982 | Schmolka | |
| 4,447,336 A | 5/1984 | Vandersall | |
| 4,447,337 A | 5/1984 | Adl et al. | |
| 4,606,831 A | 8/1986 | Kegeler et al. | |
| 4,754,027 A | 6/1988 | Applegren | |
| 5,037,647 A | 8/1991 | Chowhan et al. | |
| 5,075,400 A | 12/1991 | Andrade et al. | |
| 5,233,032 A | 8/1993 | Zody et al. | |
| 5,277,911 A | 1/1994 | Viegas et al. | |
| 5,315,003 A | 5/1994 | Maruyama et al. | |
| 5,342,620 A | 8/1994 | Chowhan | |
| 5,370,744 A | 12/1994 | Chowhan et al. | |
| 5,376,693 A | 12/1994 | Viegas et al. | |
| 5,480,633 A | 1/1996 | Simion et al. | |
| 5,489,674 A | 2/1996 | Yeh | |
| 5,505,953 A | 4/1996 | Chowhan | |
| 5,536,825 A | 7/1996 | Yeh et al. | |
| 5,631,005 A | 5/1997 | Dassanayake et al. | |
| 5,756,443 A | 5/1998 | Inoue et al. | |
| 5,756,720 A | 5/1998 | Chowdhary | |
| 5,773,396 A | 6/1998 | Zhang et al. | |
| 5,811,466 A | 9/1998 | Chowhan et al. | |
| 5,981,255 A | 11/1999 | Miyota et al. | |
| 5,997,907 A | 12/1999 | Goswami et al. | |
| 6,004,923 A | 12/1999 | Oftring et al. | |
| 6,057,283 A | 5/2000 | Oftring et al. | |
| 6,063,402 A | 5/2000 | Gebert et al. | |
| 6,139,794 A | 10/2000 | Asgharian et al. | |
| 6,143,799 A | 11/2000 | Chowhan et al. | |
| 6,204,238 B1 | 3/2001 | Oftring et al. | |
| 6,214,596 B1 | 4/2001 | Asgharian et al. | |
| 6,319,464 B1 | 11/2001 | Asgharian | |
| 6,320,064 B1 | 11/2001 | Oftring et al. | |
| 6,365,636 B1 | 4/2002 | Chowhan et al. | |
| 6,403,609 B1 | 6/2002 | Asgharian | |
| 6,503,497 B2 | 1/2003 | Chowhan et al. | |
| 6,583,124 B2 * | 6/2003 | Asgharian ................... | 514/54 |
| 6,656,504 B1 | 12/2003 | Bosch et al. | |
| 6,664,294 B1 | 12/2003 | Park et al. | |
| 6,664,381 B1 | 12/2003 | Wielinga | |
| 6,849,253 B2 | 2/2005 | Chowhan et al. | |
| 7,282,178 B2 | 10/2007 | Salamone et al. | |
| 2002/0064514 A1 | 5/2002 | Viegas et al. | |
| 2002/0141899 A1 | 10/2002 | Tsao | |
| 2004/0052746 A1 | 3/2004 | Tamareselvy et al. | |
| 2004/0241130 A1 | 12/2004 | Tamareselvy et al. | |
| 2005/0250661 A1 | 11/2005 | Bragulla et al. | |
| 2006/0027364 A1 | 2/2006 | Kelly et al. | |
| 2008/0138310 A1 | 6/2008 | Ketelson et al. | |

FOREIGN PATENT DOCUMENTS

| | | |
|---|---|---|
| EP | 0277499 | 8/1988 |
| EP | 0207045 | 9/1991 |

(Continued)

OTHER PUBLICATIONS

Bedells et al., "Micellisation of Diblock Copoly(oxyethylene/oxybutylene) in Aqueous Solution" J. Chem. Soc. Faraday Trans; vol. 89(8):1235-1242, 1993.

(Continued)

*Primary Examiner* — Zohreh Fay

(57) ABSTRACT

The present invention relates to compositions comprising ethyleneoxide butyleneoxide and a galactomannan such as guar. The compositions are particularly well suited for ophthalmic applications such as contact lens disinfection and rewetting. Methods for the treatment of dry eye using the compositions of the present invention are also contemplated.

10 Claims, 29 Drawing Sheets

(56) References Cited

FOREIGN PATENT DOCUMENTS

| | | |
|---|---|---|
| EP | 0557627 | 9/1993 |
| EP | 0514890 | 9/1996 |
| EP | 0686643 | 6/2001 |
| EP | 1203808 A1 | 5/2002 |
| EP | 0732342 | 8/2002 |
| EP | 0934343 | 1/2003 |
| EP | 1203808 B1 | 9/2004 |
| EP | 01630176 | 3/2006 |
| GB | 722746 | 1/1955 |
| JP | 55094901 | 7/1980 |
| JP | 63035606 | 2/1988 |
| JP | 63101402 | 5/1988 |
| JP | 01247049 | 10/1989 |
| JP | 05239105 | 9/1993 |
| JP | 05239106 | 9/1993 |
| TW | 446752 B | 7/2001 |
| TW | 200839346 | 10/2008 |
| WO | 97/11974 | 4/1997 |
| WO | 97/25354 | 7/1997 |
| WO | 98/18828 | 5/1998 |
| WO | 98/40108 | 9/1998 |
| WO | 99/06023 | 2/1999 |
| WO | 99/06512 | 2/1999 |
| WO | 03/008456 | 1/2003 |
| WO | 03/043668 | 5/2003 |
| WO | 2006/017623 | 2/2006 |
| WO | 2006/026166 | 3/2006 |
| WO | 2006/110482 | 10/2006 |
| WO | 2008/073909 | 6/2008 |
| WO | 2008/144494 | 11/2008 |
| WO | 2009/132294 | 10/2009 |
| WO | 2010/030785 | 3/2010 |

OTHER PUBLICATIONS

Chaibundit, et al.; Association Properties of Triblock Copolymers in Aqueous Solution: Copolymers of Ethylene Oxide and 1,2-Butylene Oxide with Long E-blocks; Langmuir; vol. 16:9645-9652, 2000.

Cheng et al., Preparation and Characterization of Molecular Weight Fractions of Guar Galactomannans Using Acid and Enzymatic Hydrolysis, International Journal of Biological Macromolecules, vol. 31:29-35, 2002.

Feng et al., Colloids & Surfaces A: Physiochemical Eng Aspects, vol. 317:535-542, 2008.

Garcia et al., "Caracteristicas y Aplicaciones de la Goma Guar," Ciencia y Technologia Pharamaceutica, vol. 15 (1):3-10, 2005.

Gebert et al., "Purified Guar Galactomannan as an Improved Pharmaceutical Excipient," Pharmaceutical Development and Technology, vol. 3(3):315-323, 1998.

Gittings et al., "The Effect of Solvent and Ions on the Structure and Rheological Prpoerties of Guar Solutions", J. Phys Chemistry A., vol. 105:9310-9315, 2001.

Kelarakis et al., "Temperature Dependencies of the Critical Micelle Concentrations of Diblock Oxyethylene/Oxybutylene Copolymers. A Case of Athermal Micellization", Macromolecules; vol. 31:944-946, 1998.

Ketelson et al., "Dynamic Wettability Properties of a Soft Contact Lens Hydrogel", Colloids and Surfaces B: Biointerfaces; vol. 40:1-9, 2005.

Kulkarni et al., "Rheological Properties of the Dispersions of Starch, Guar Gum, and Their Physical Mixtures in the Temperature Interval 298.15-333.15 K," Polym.-Plast. Technol. Eng., vol. 39(3):437-456, 2000.

Lapasin et al., "Rheology of Hydroxyethyl Guar Gum Derivatives," Carbohydrate Polymers, vol. 14:411-427, 1991.

Leiske et al., "Investigation of an Amphiphilic Block Copolymer to Prevent Contact Lens Fouling", ARVO, Program No. 5646/D955, 2009.

Nace, V.M., "Contrasts in the Surface Activity of Polyoxypropylene and Polyoxybutylene-based Block Copolymer Surfactants", Journal American Oil Chemical Society, vol. 73(1):1-9, 1996.

Tantry et al., "Rheological Study of Guar Gum," Indian Journal of Pharmaceutical Sciences, pp. 74-76, Jan.-Feb. 2001.

Venkataiah et al., "Rheological Properties of Hydroxypropyl-and Sodium Carboxymethyl-Substituted Guar Gums in Aqueous Solution," Journal of Applied Science, vol. 27:1533-1548, 1982.

Wientjes, et al., "Linear Rheology of Guar Gum Solutions," Macromolecules, vol. 33:9594-9605, 2000.

Yang et al., "Effect of Block Structure on the Micellization and Gelation of Aqueous Solutions of Copolymers of Ethylene Oxide and Butylene Oxide; Macromolecules"; vol. 27:2371-2379, 1994.

Yang et al., "Micellization of Diblock and Triblock Copolymers in Aqueous Solution. New Results for Oxyethylene/Oxybutylene Copolymers E38B12 and E21B11E21. Comparison of Oxyethylene/Oxybutylene, Oxyethylene/Oxpropylene, and Oxyethylene/Alkyl Systems", Langmuir; vol. 11:4703-4711, 1995.

Yu et al., "Association of Diblock and Triblock Copolymers of Ethylene Oxide and Butylene Oxide in Aqueous Solution", Langmuir, vol. 12:3404-3412, 1996.

PCT International Search Report for corresponding International Application No. PCT/US2010/041218 with mailing date Mar. 14, 2011.

* cited by examiner

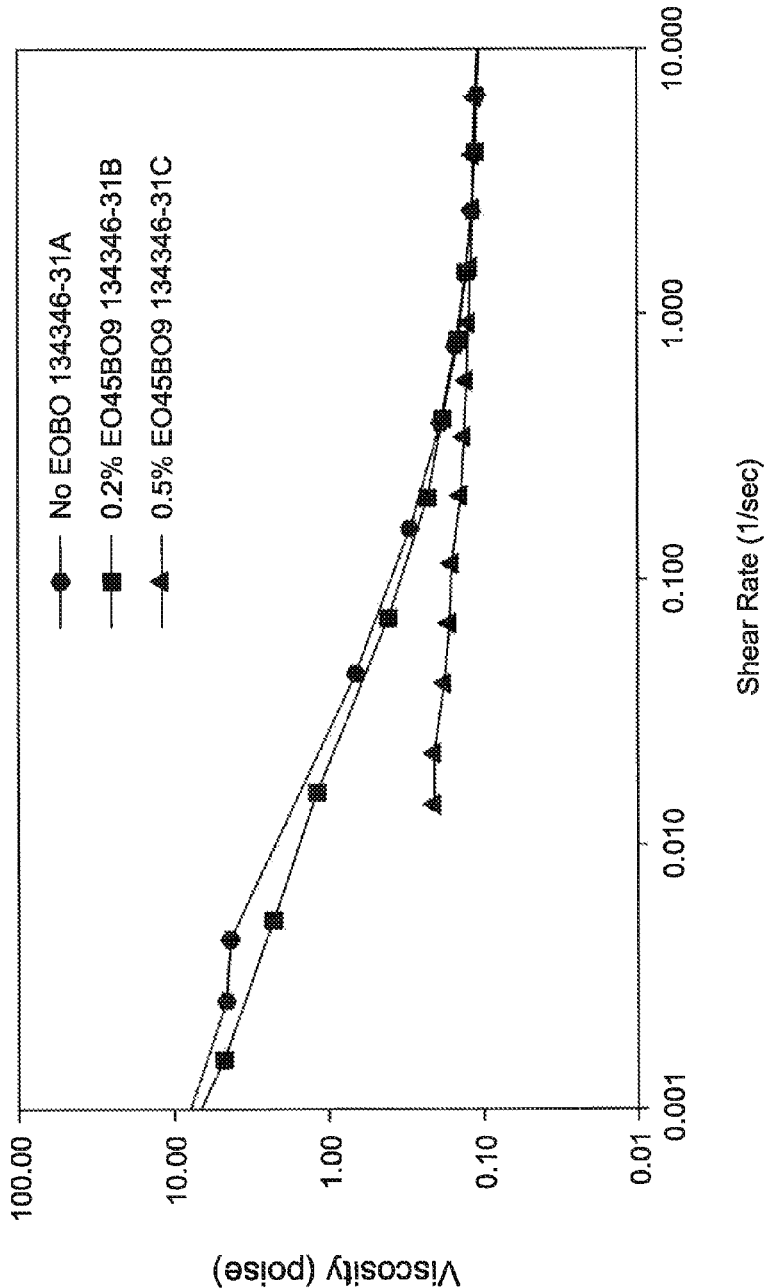

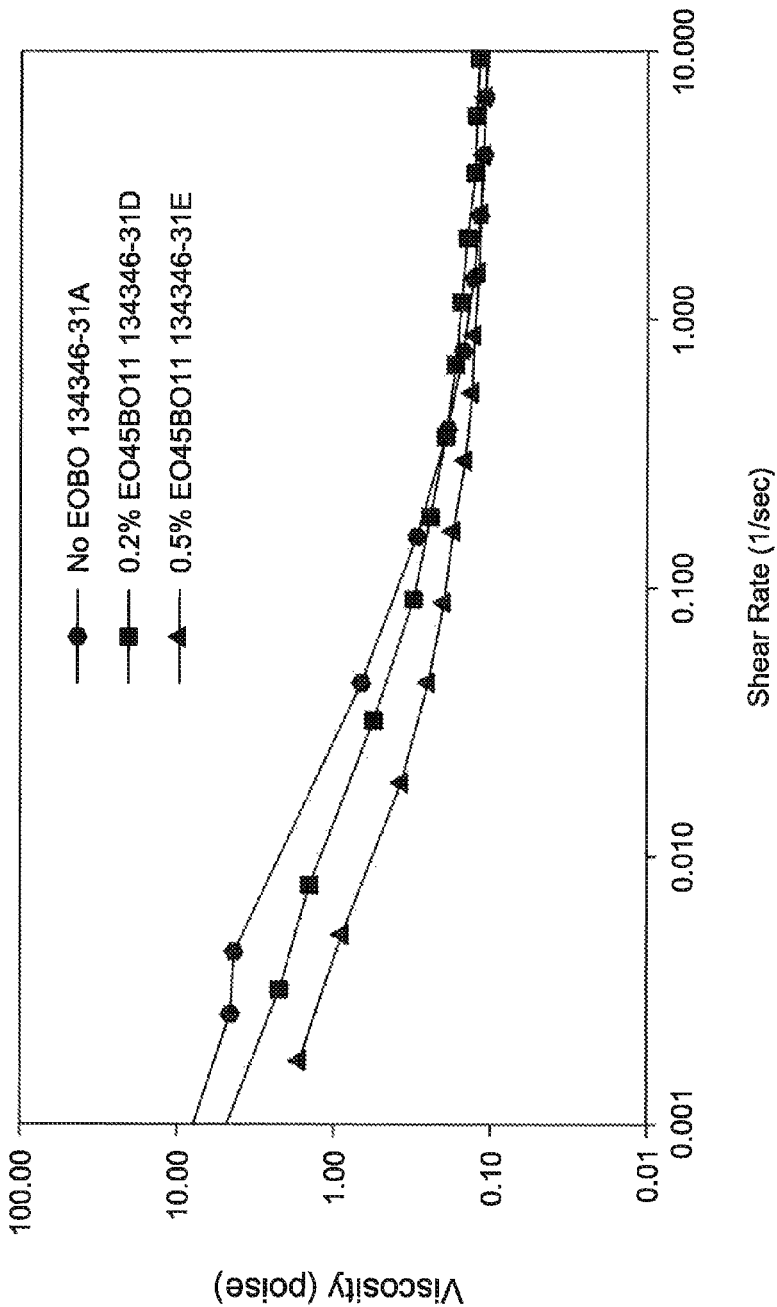

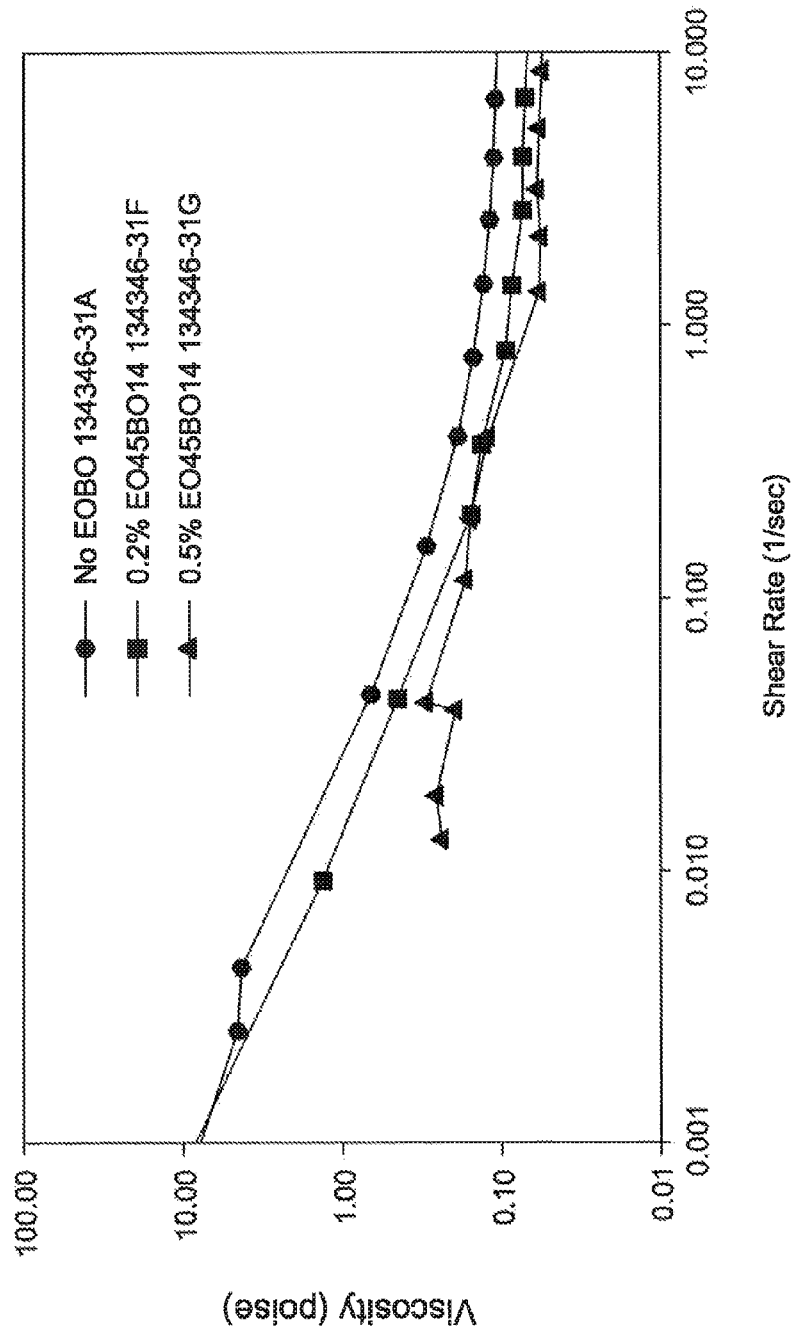

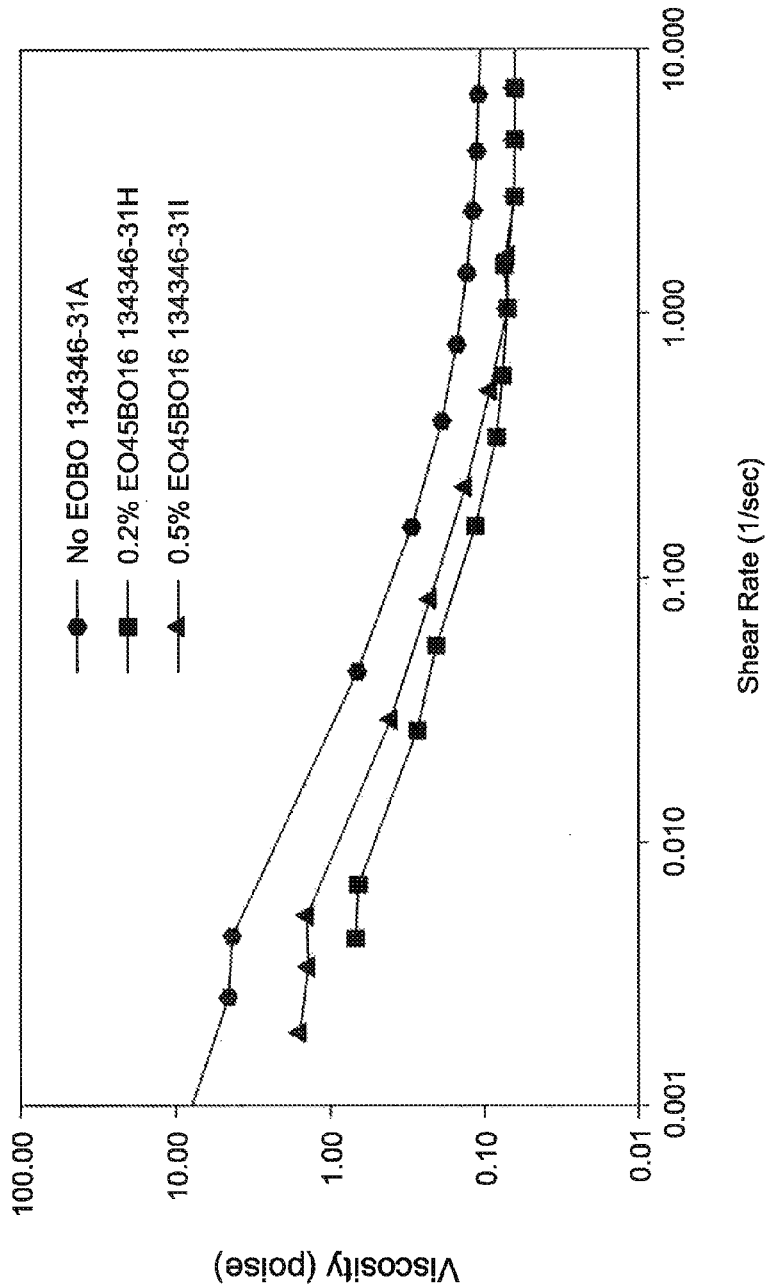

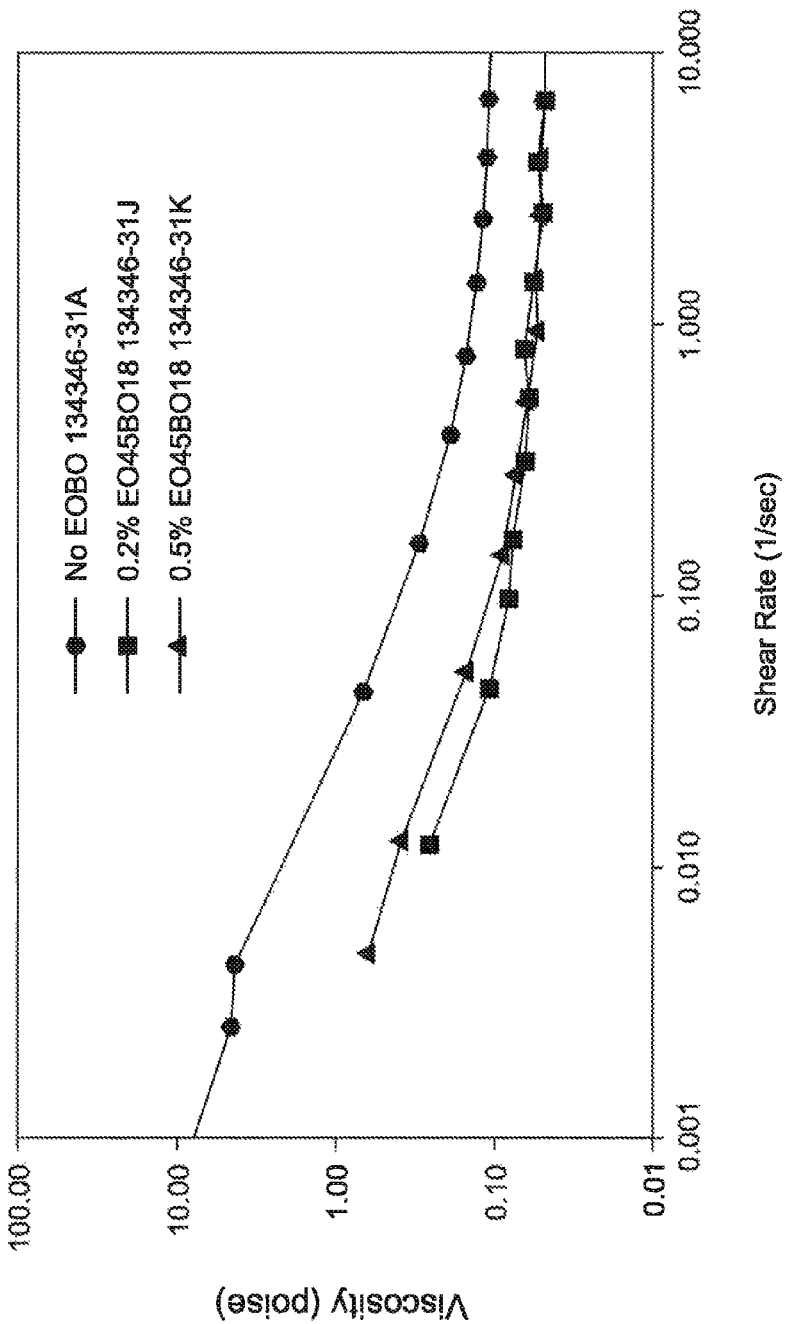

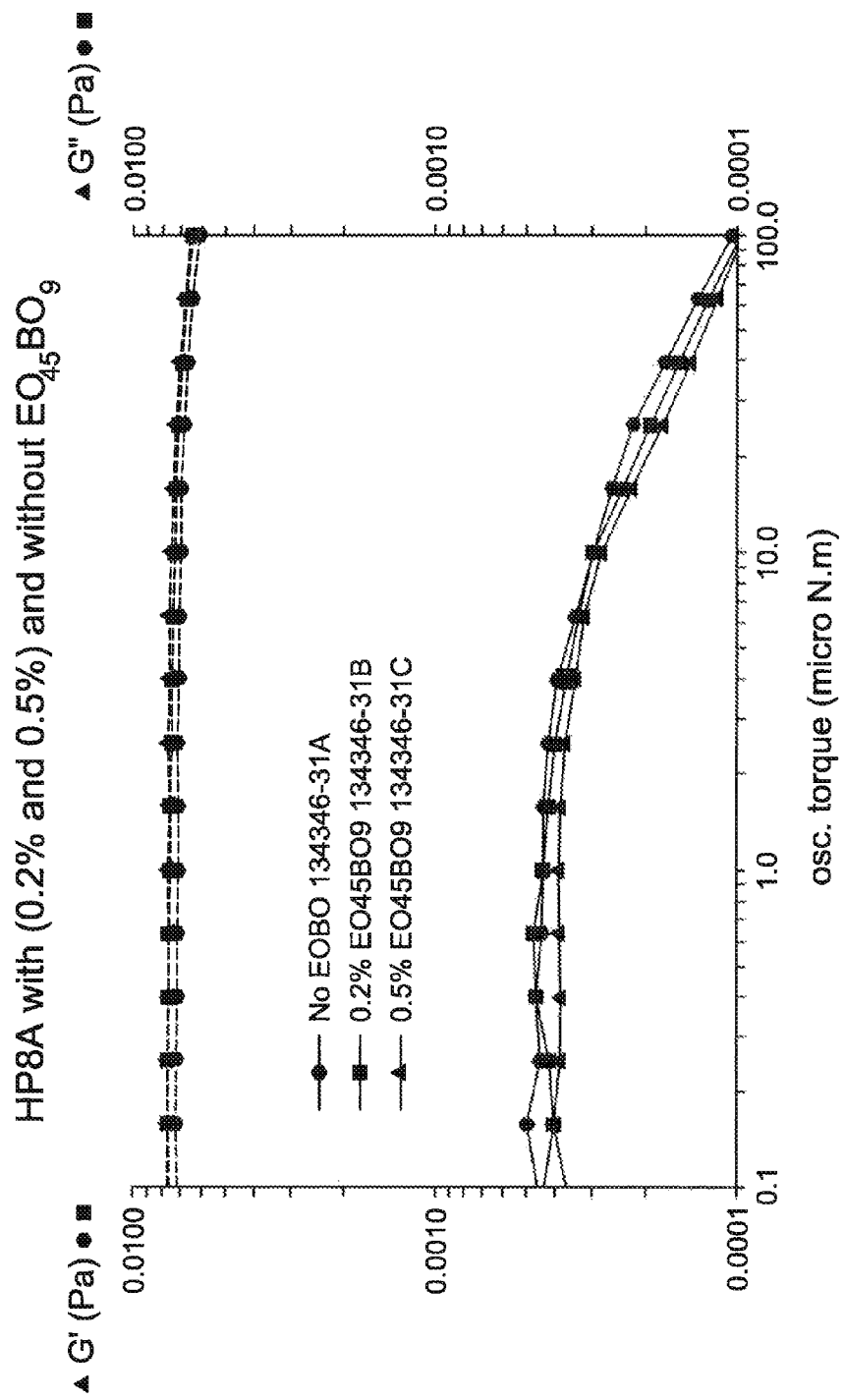

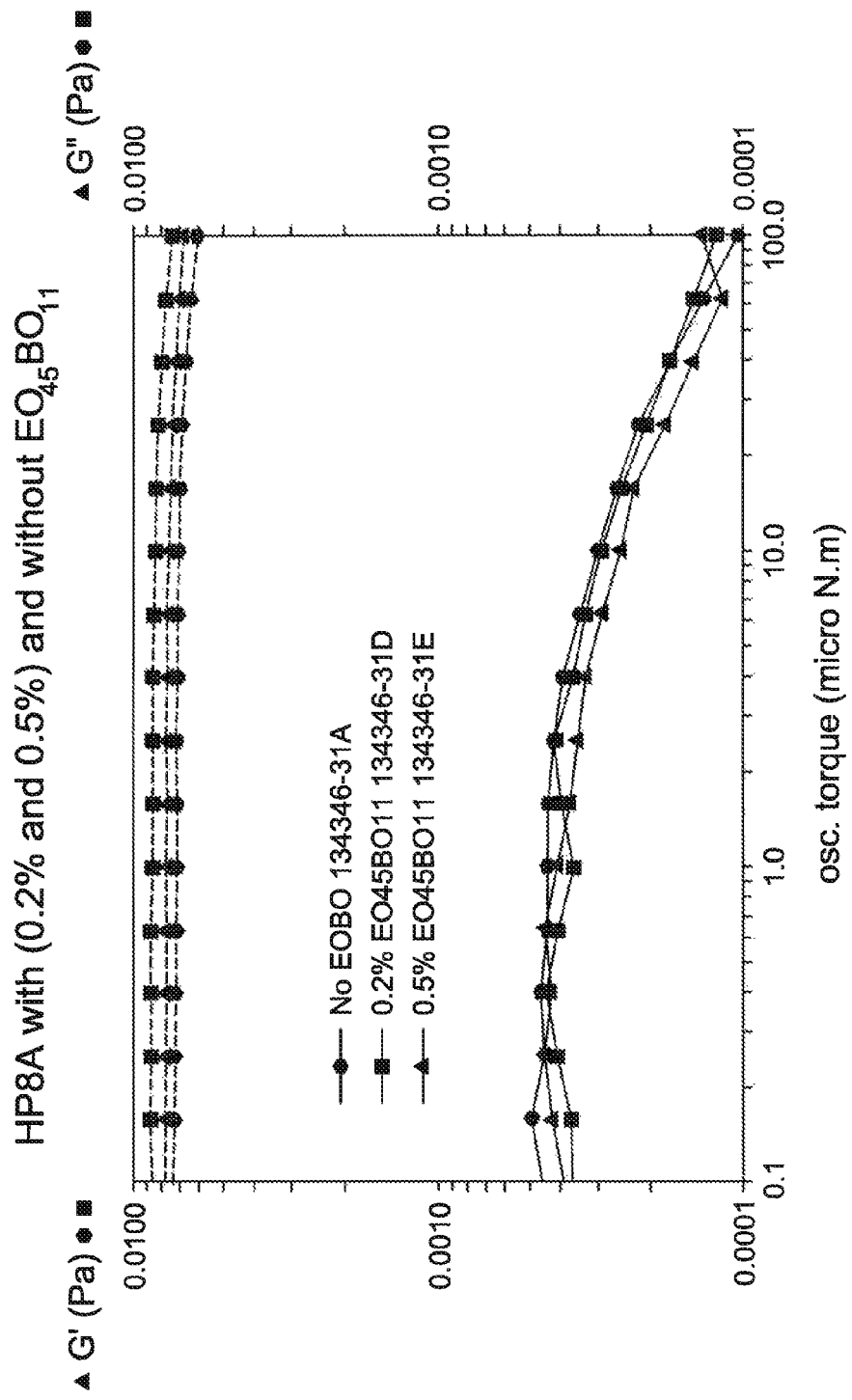

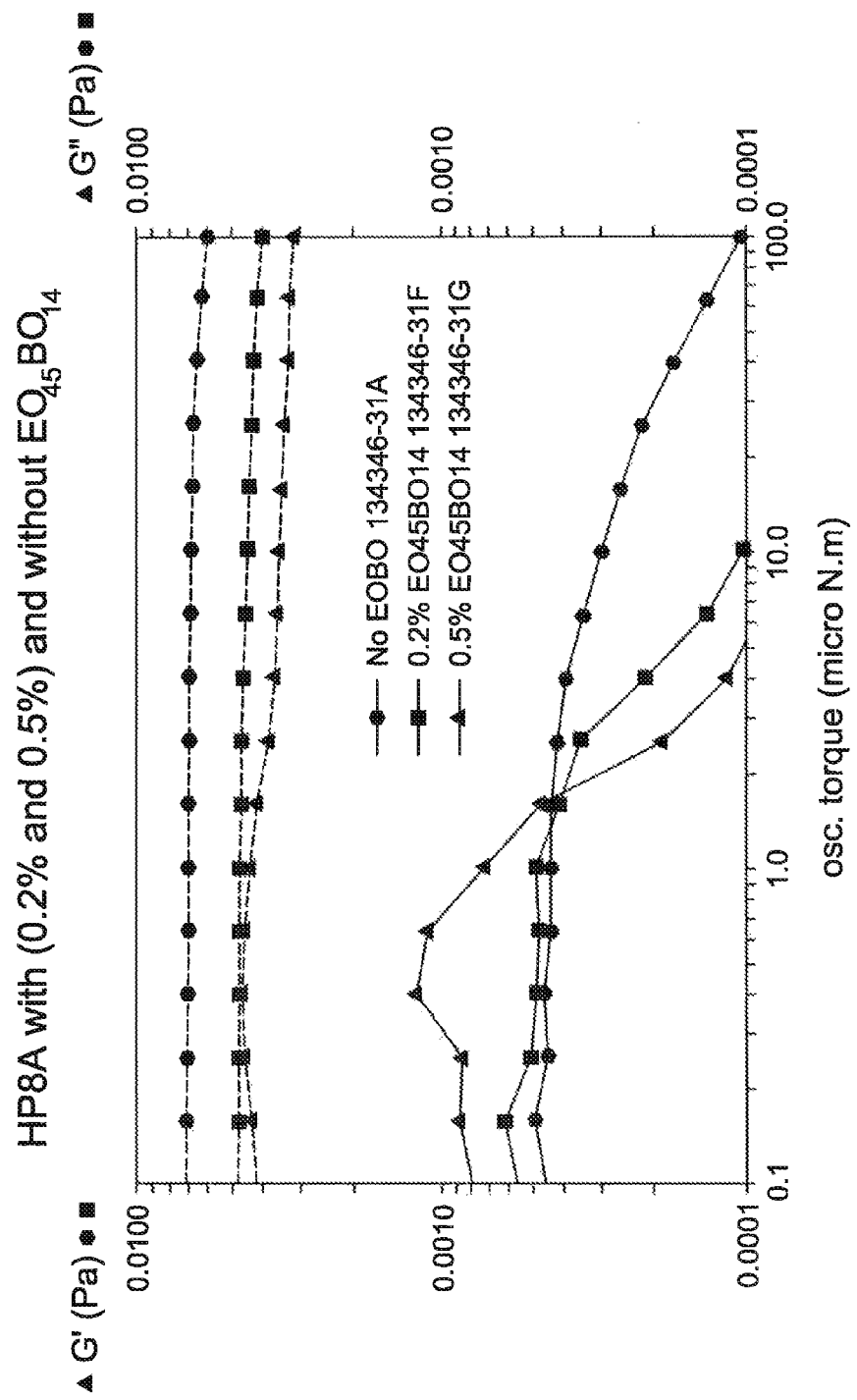

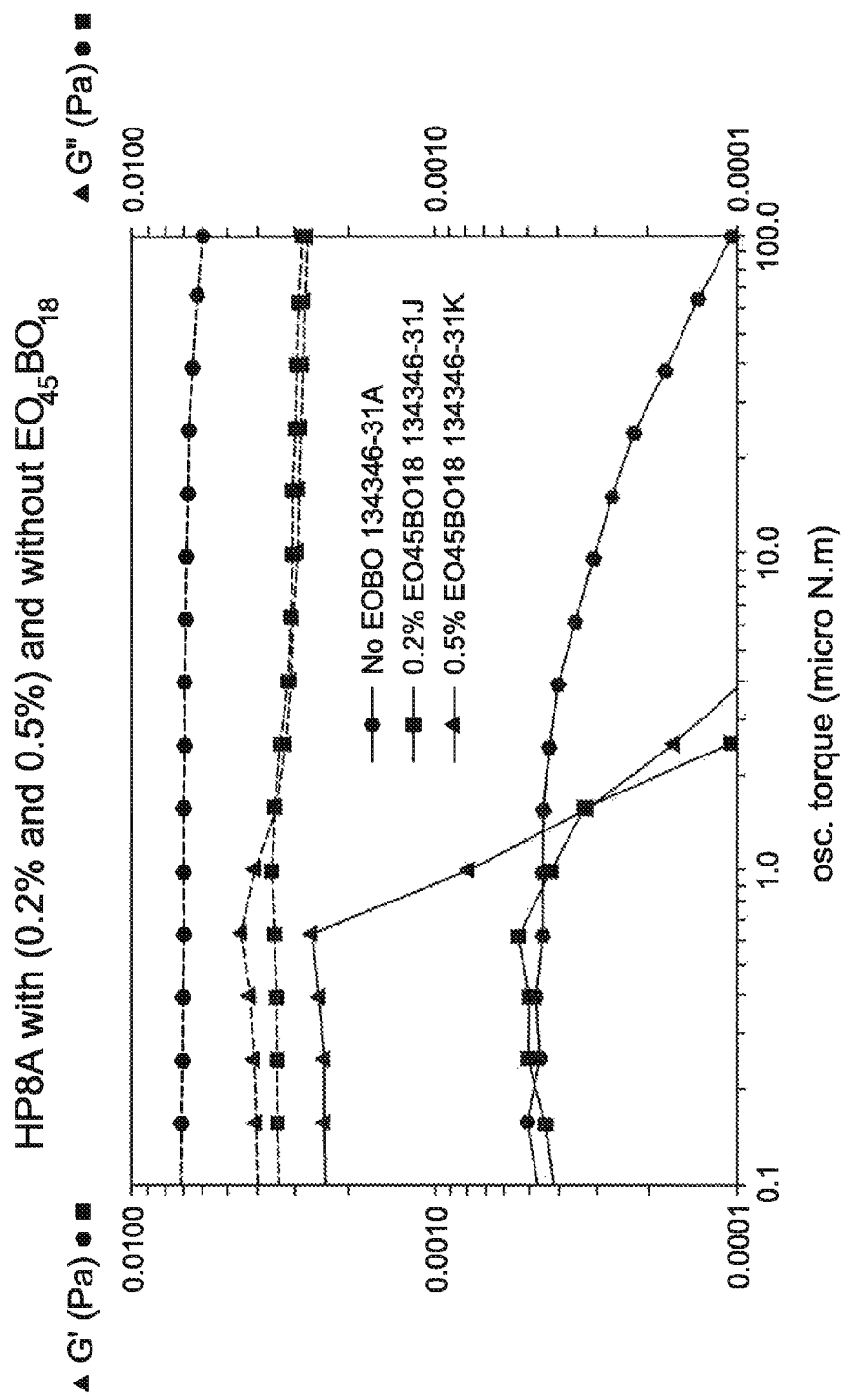

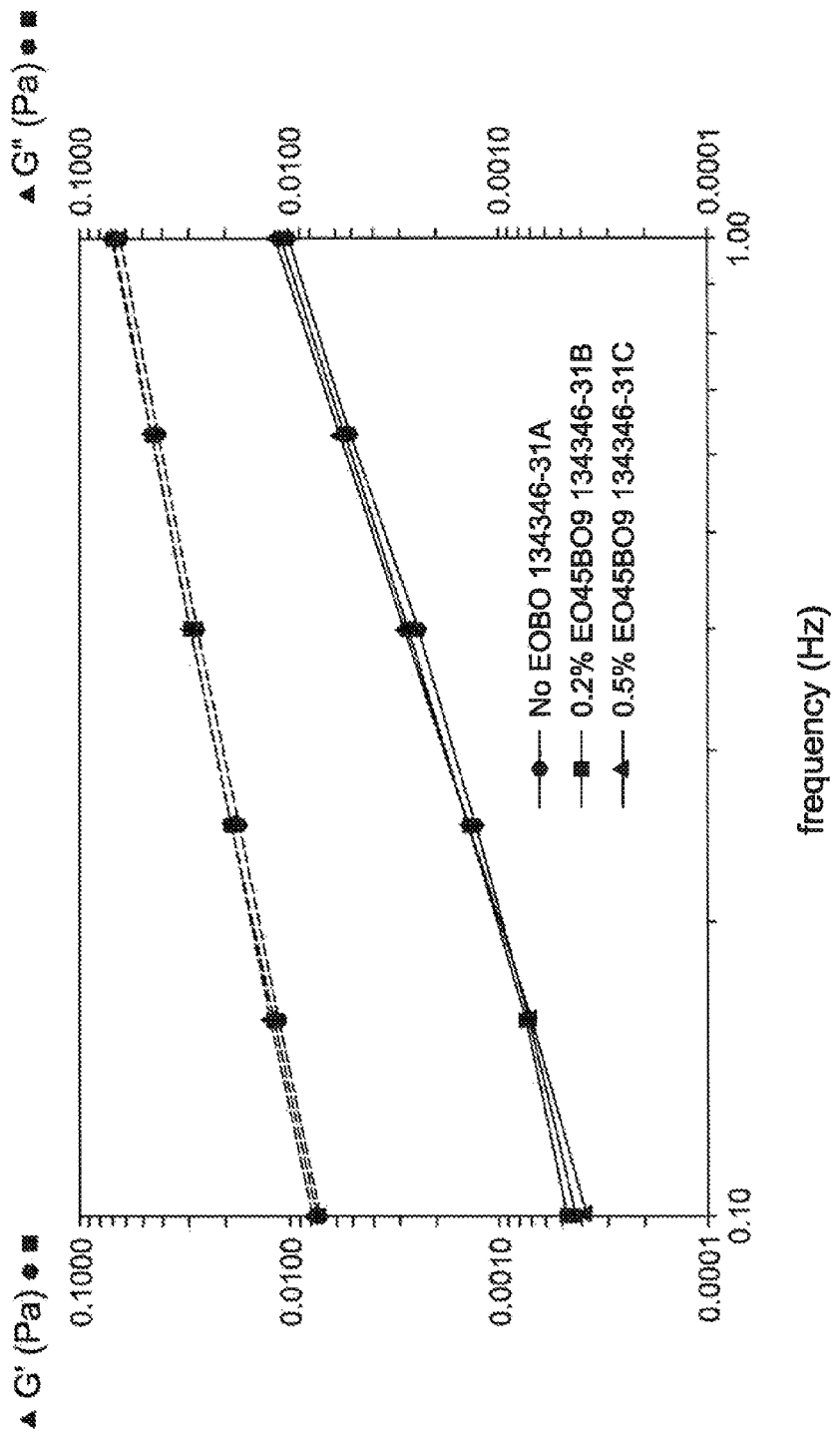

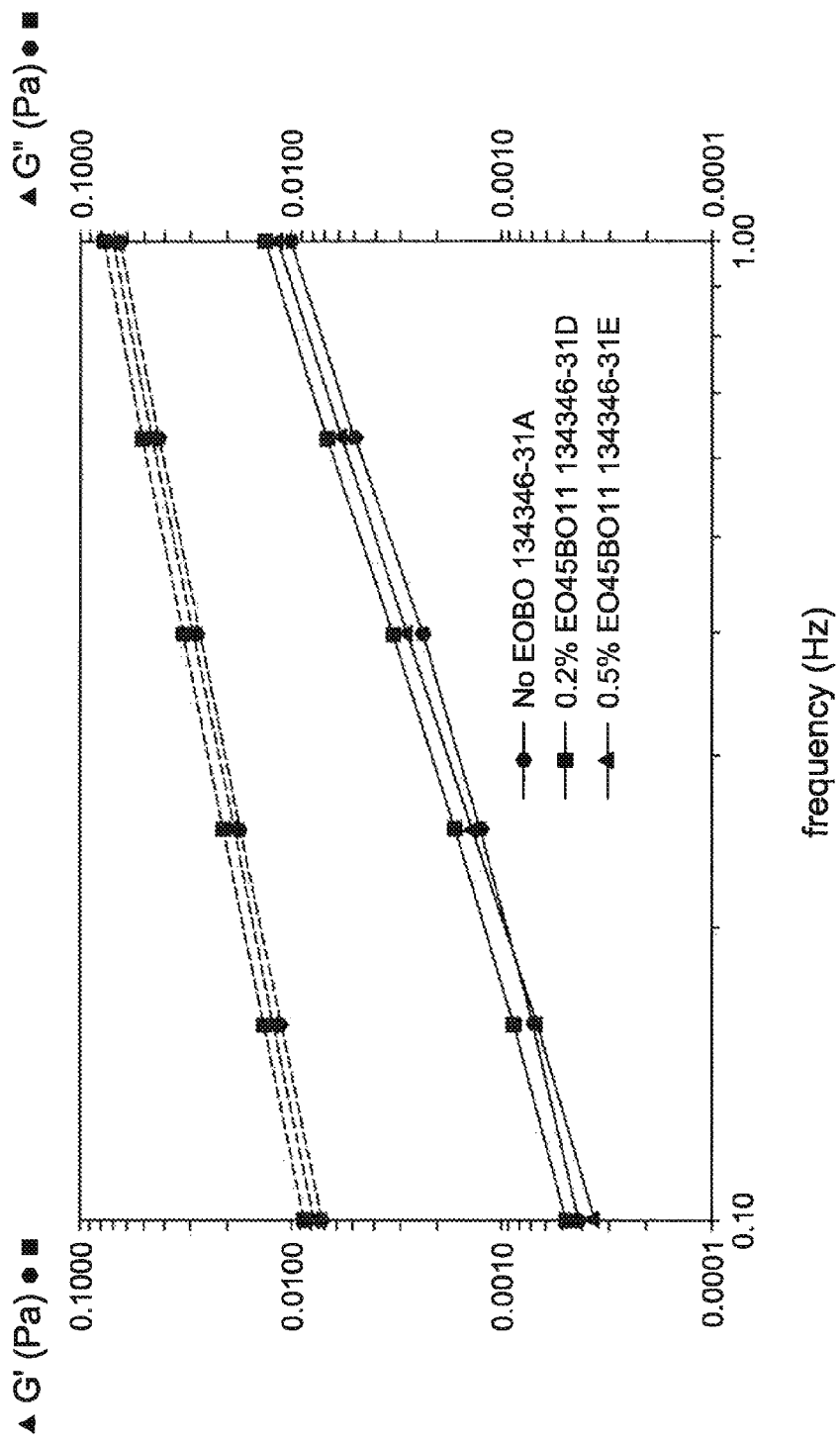

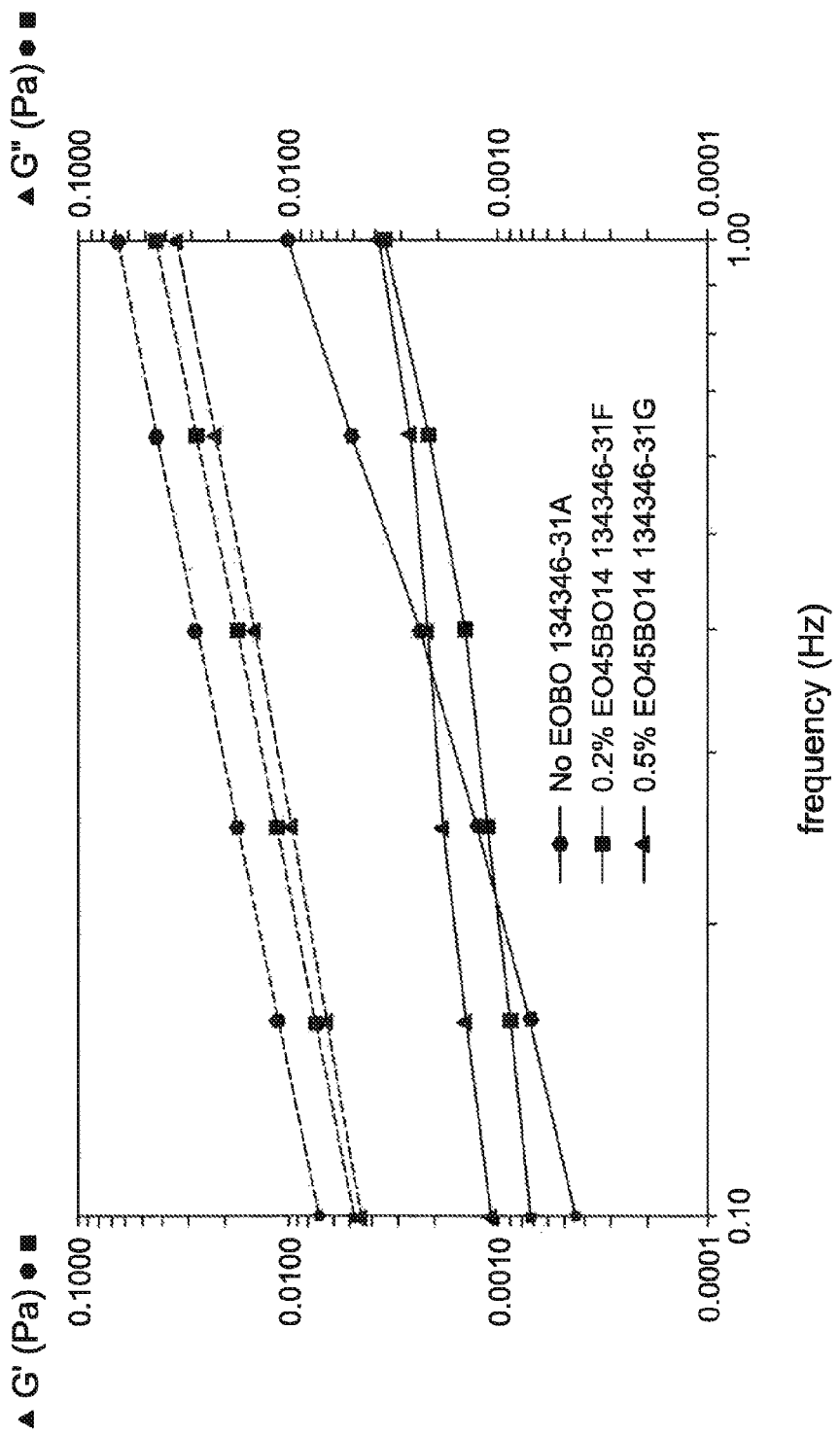

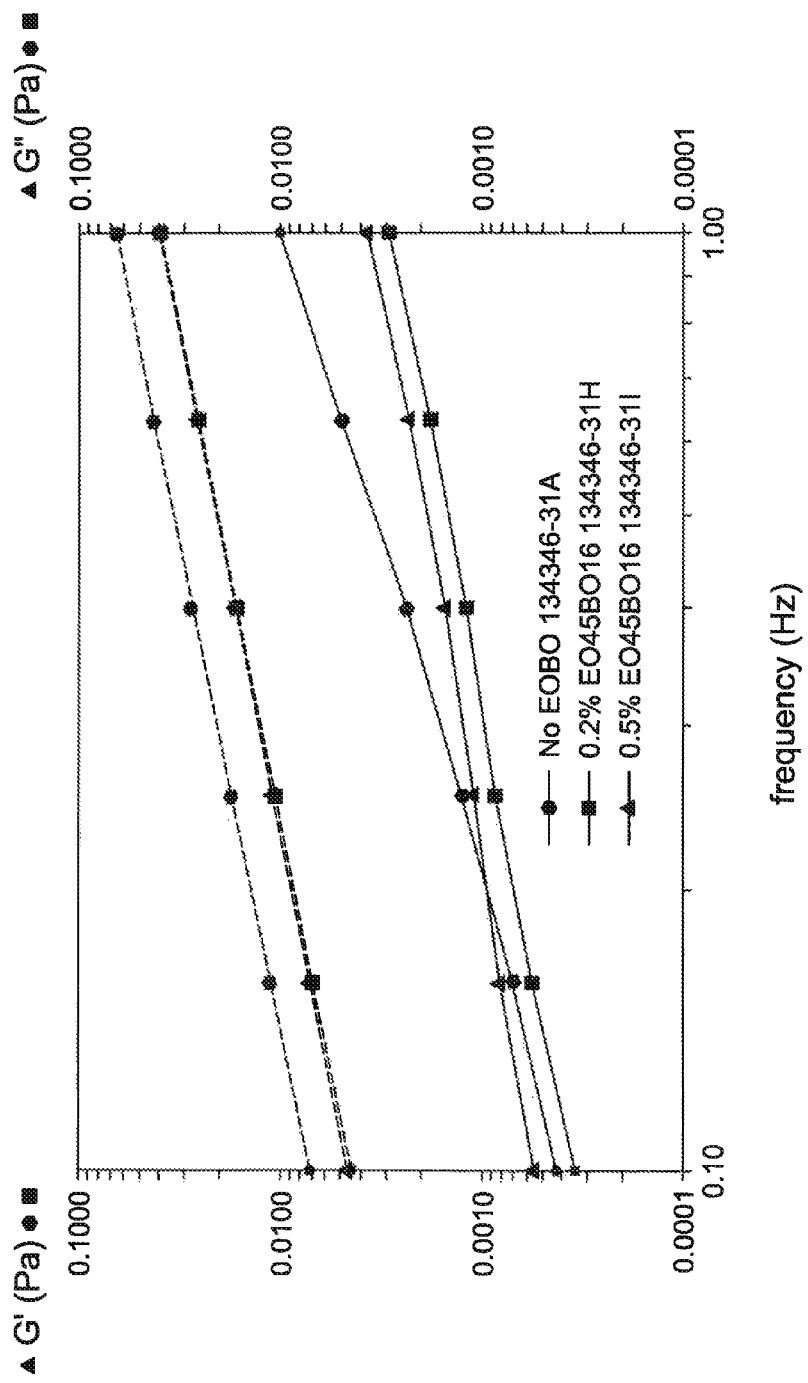

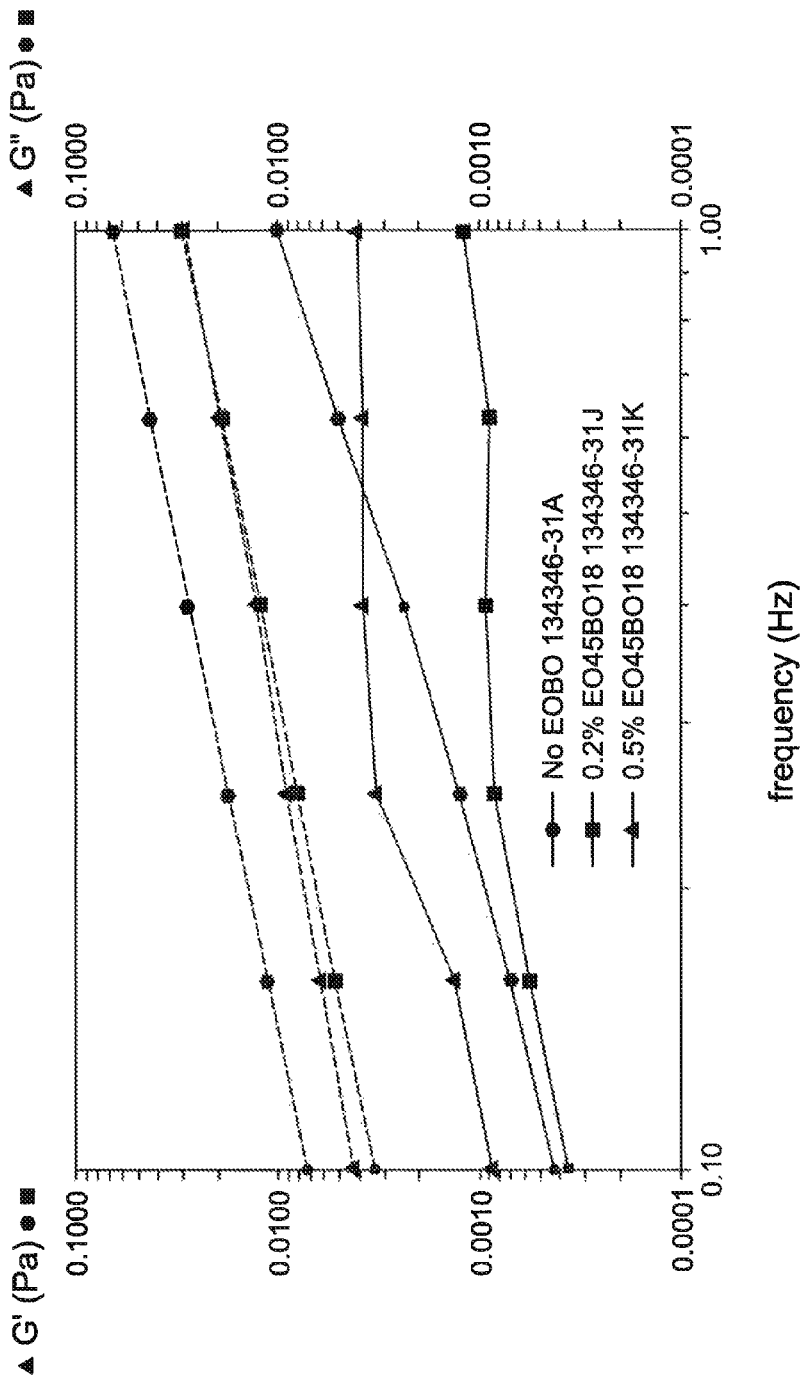

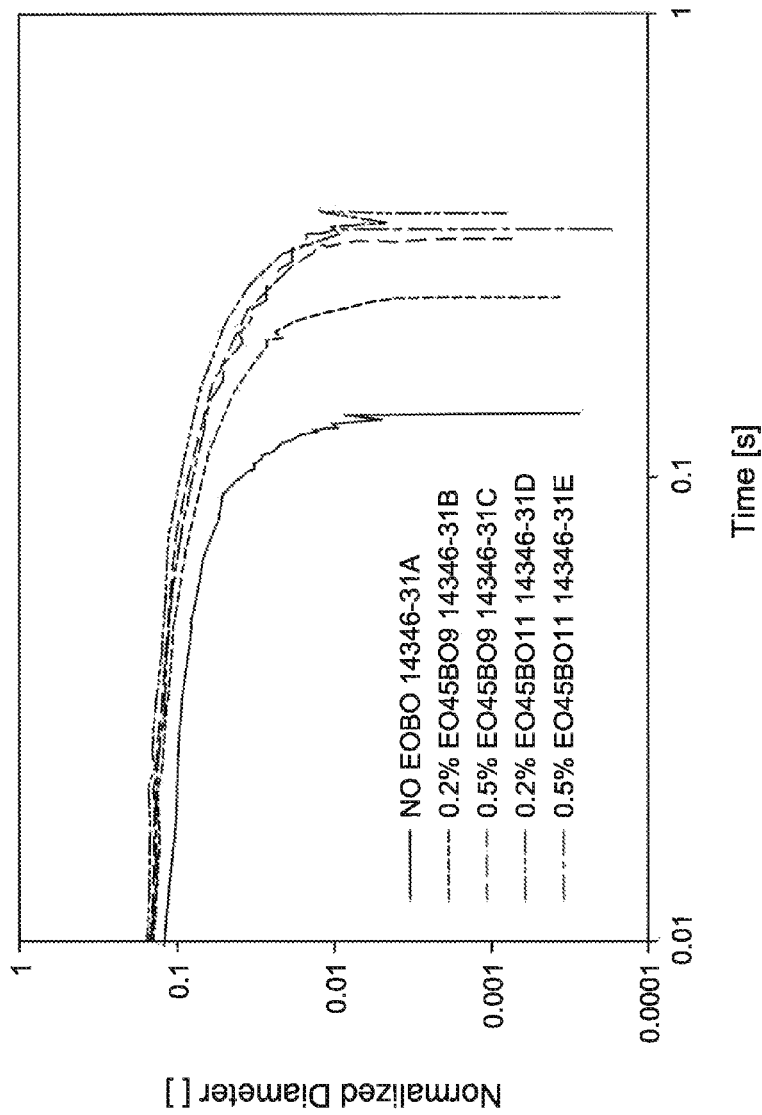

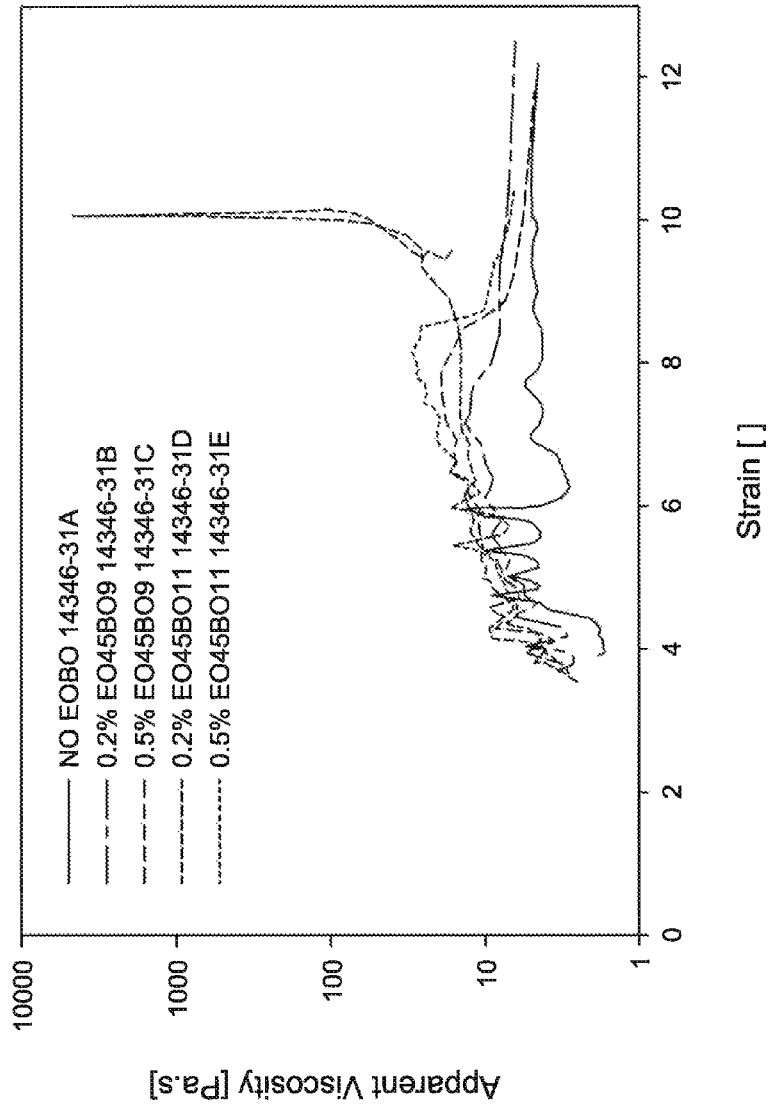

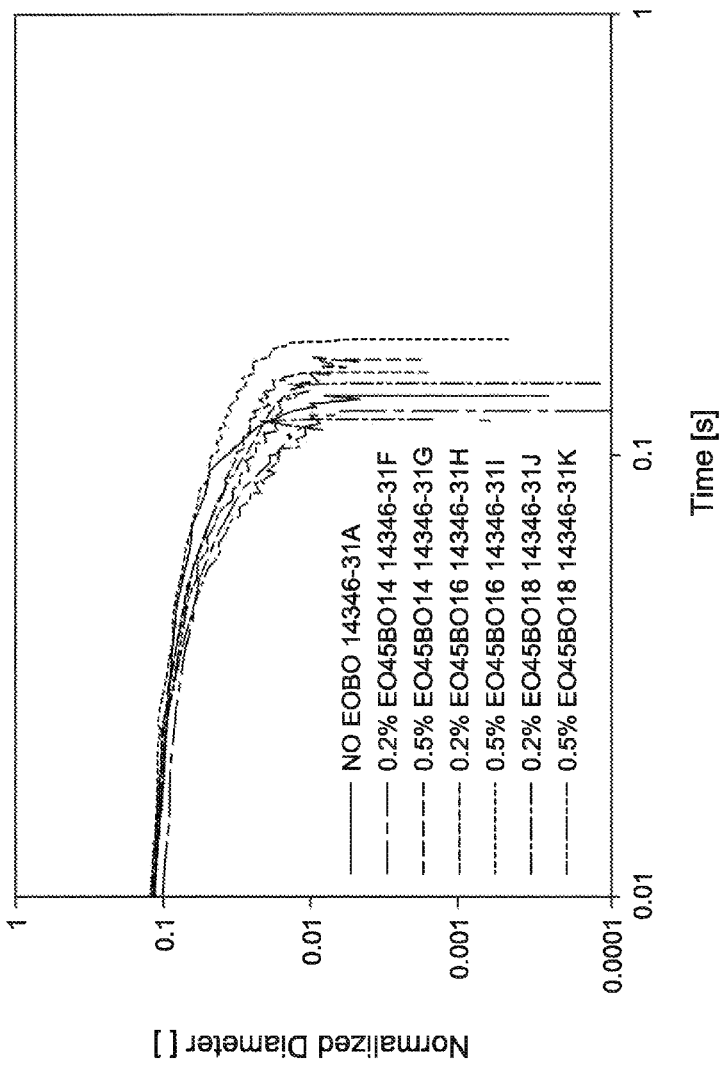

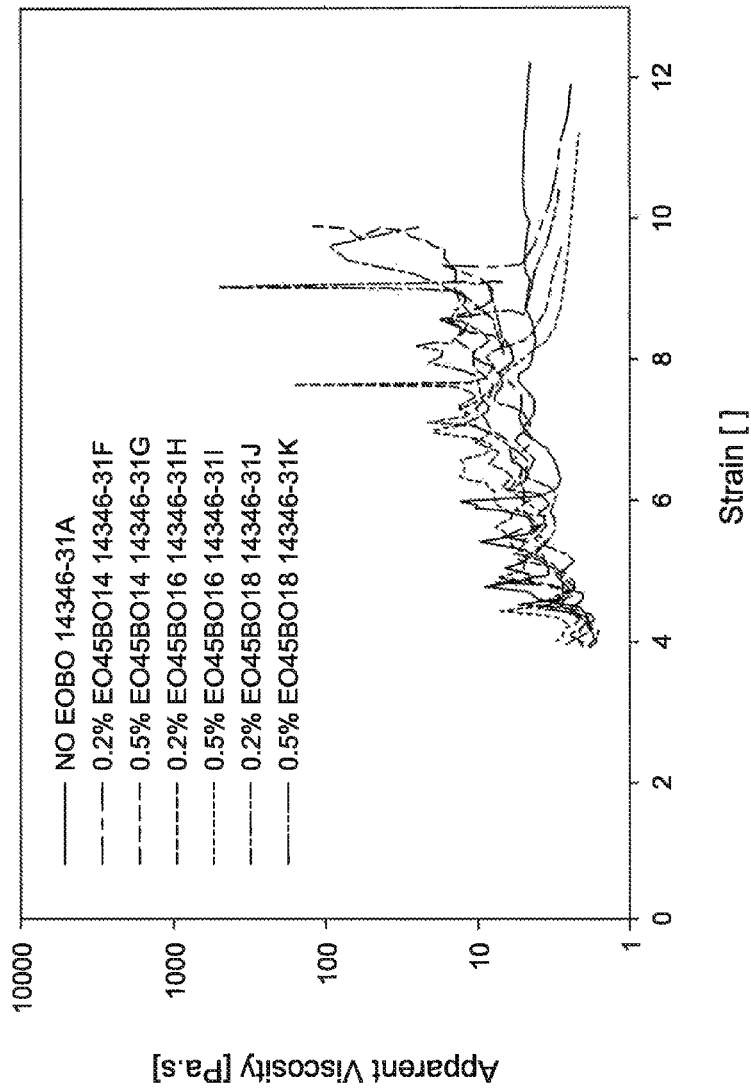

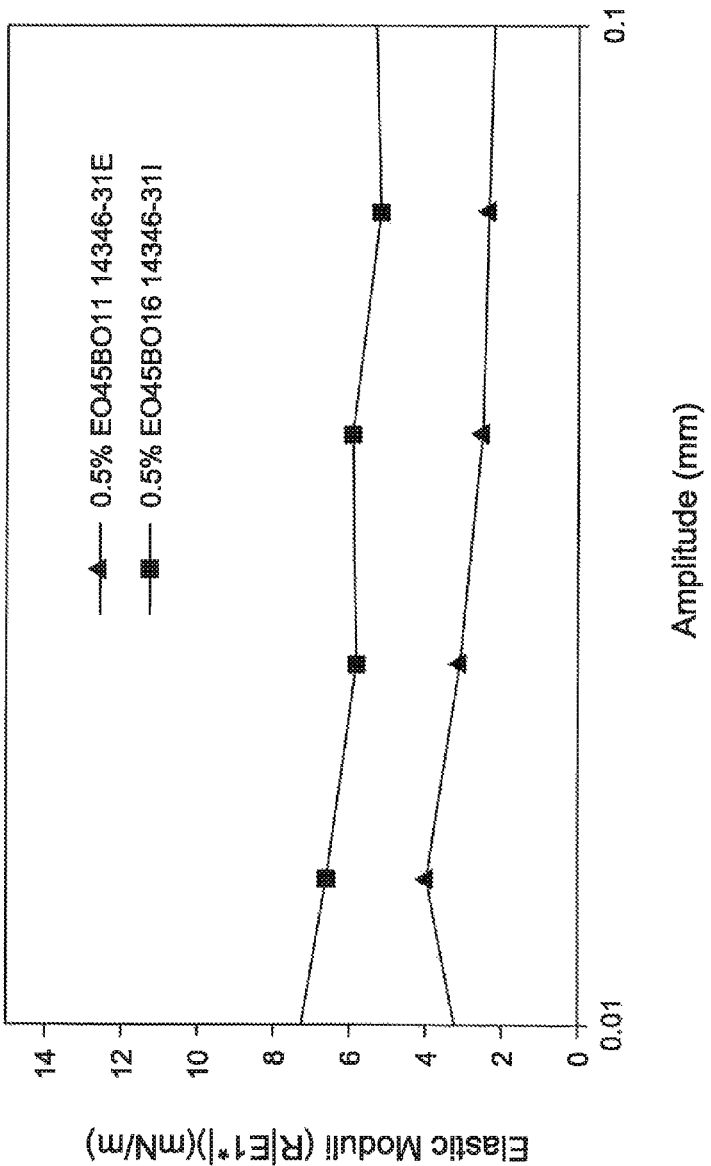
Fig. 6a Frequency Sweep For EO$_{45}$BO$_{11}$ and EO$_{45}$BO$_{16}$ with HP Guar

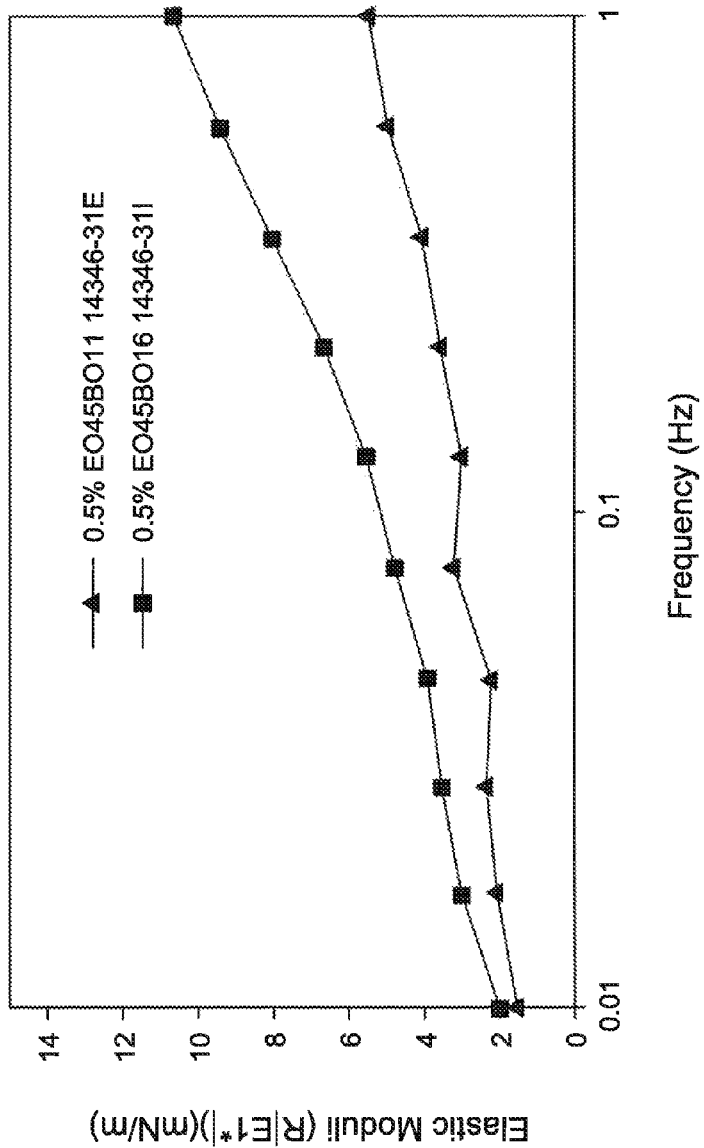
Fig. 6b Frequency Sweep For $EO_{45}BO_{11}$ and $EO_{45}BO_{16}$ with HP Guar

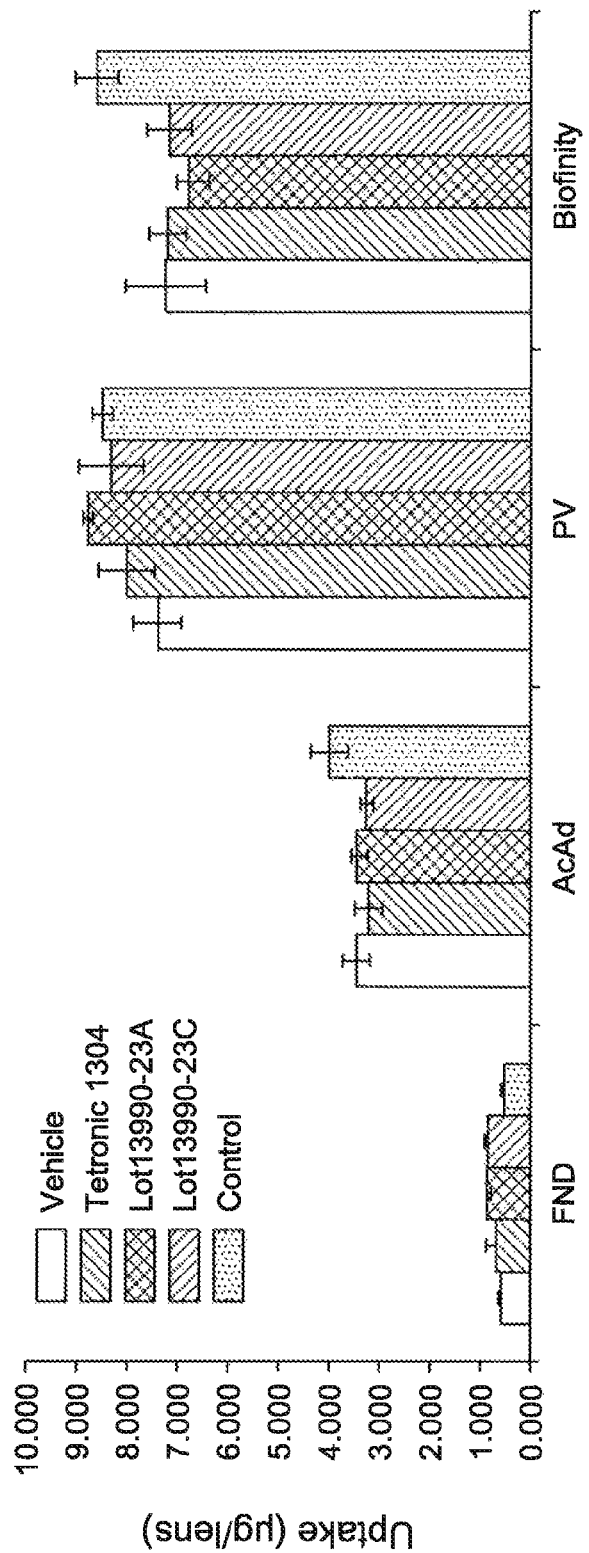

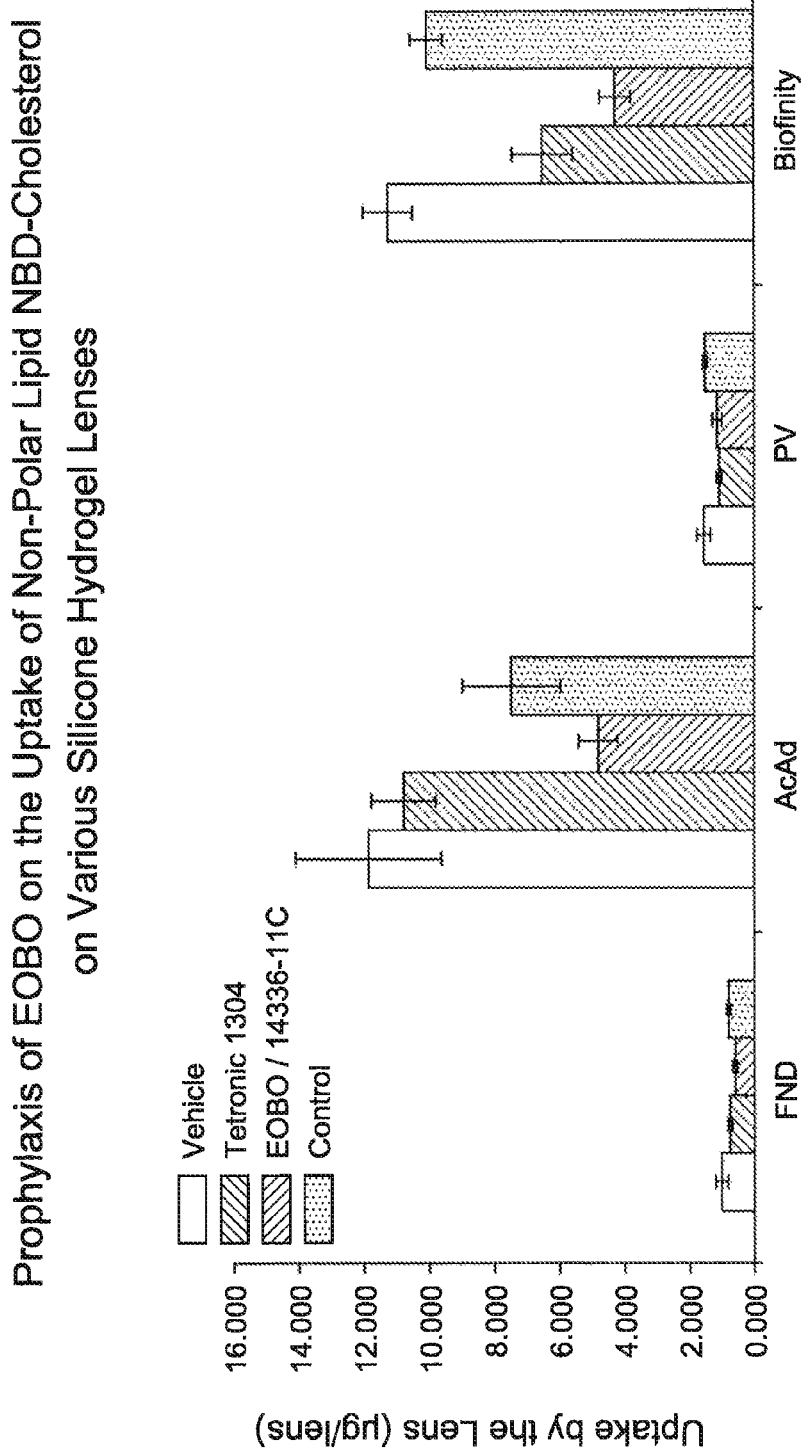

Amount Remaining of a Non-Polar Lipid (NBD-Cholesterol) on Various Silicone Hydrogel Lenses after Cleaning

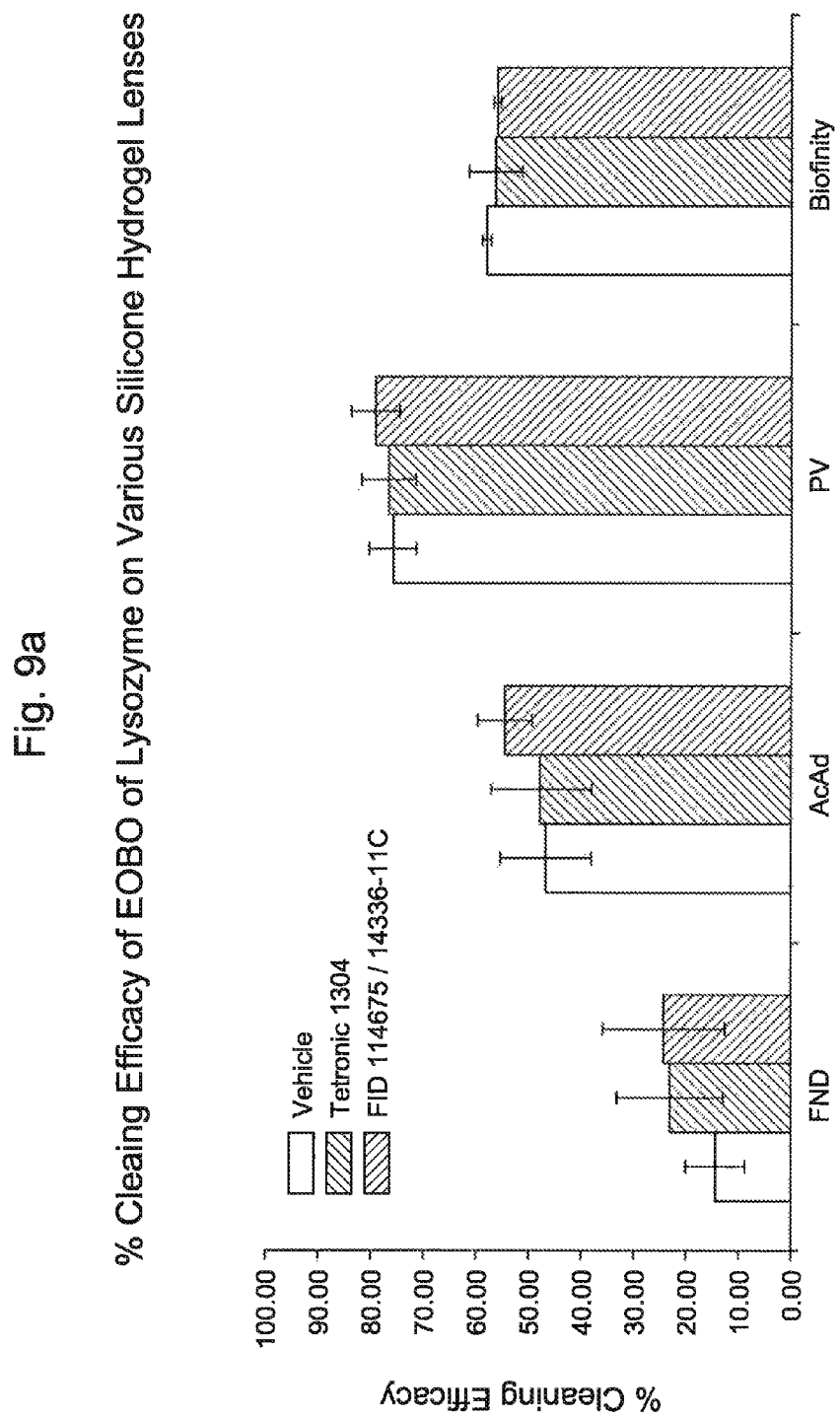

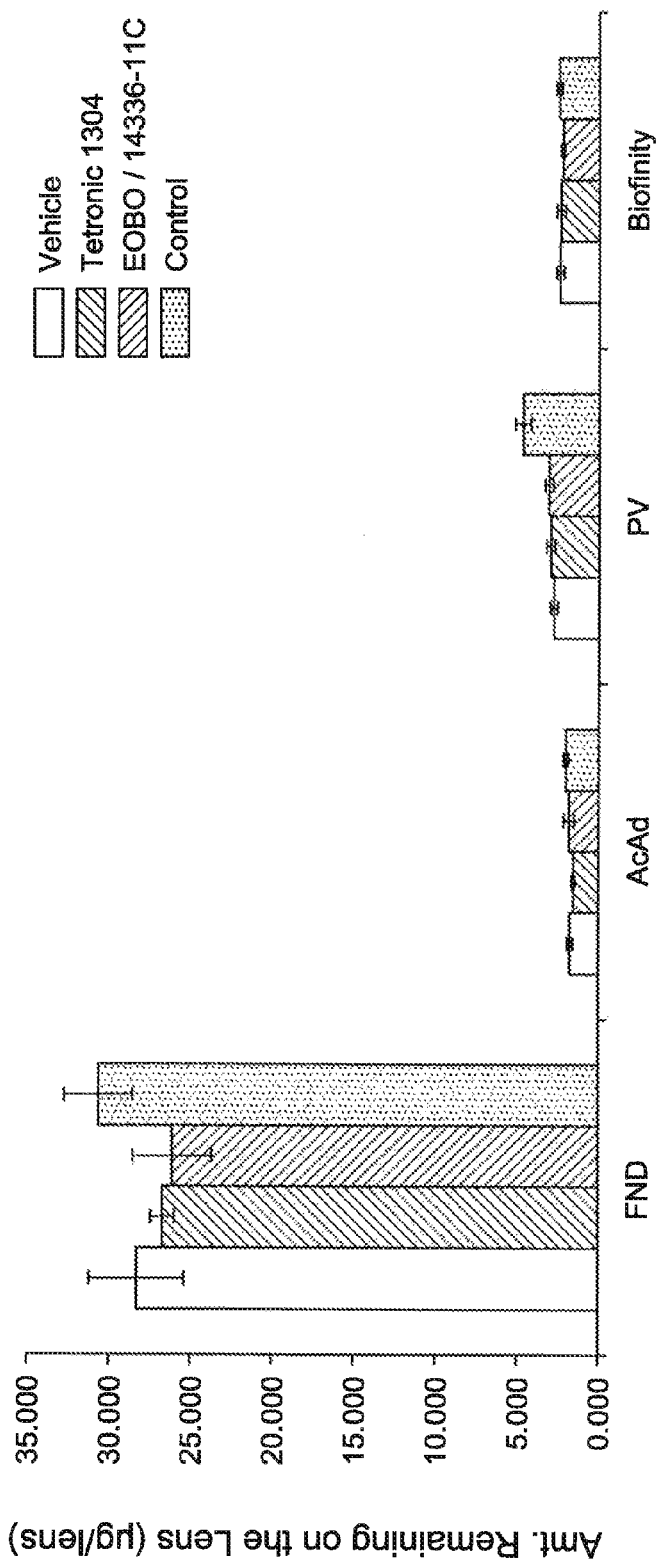

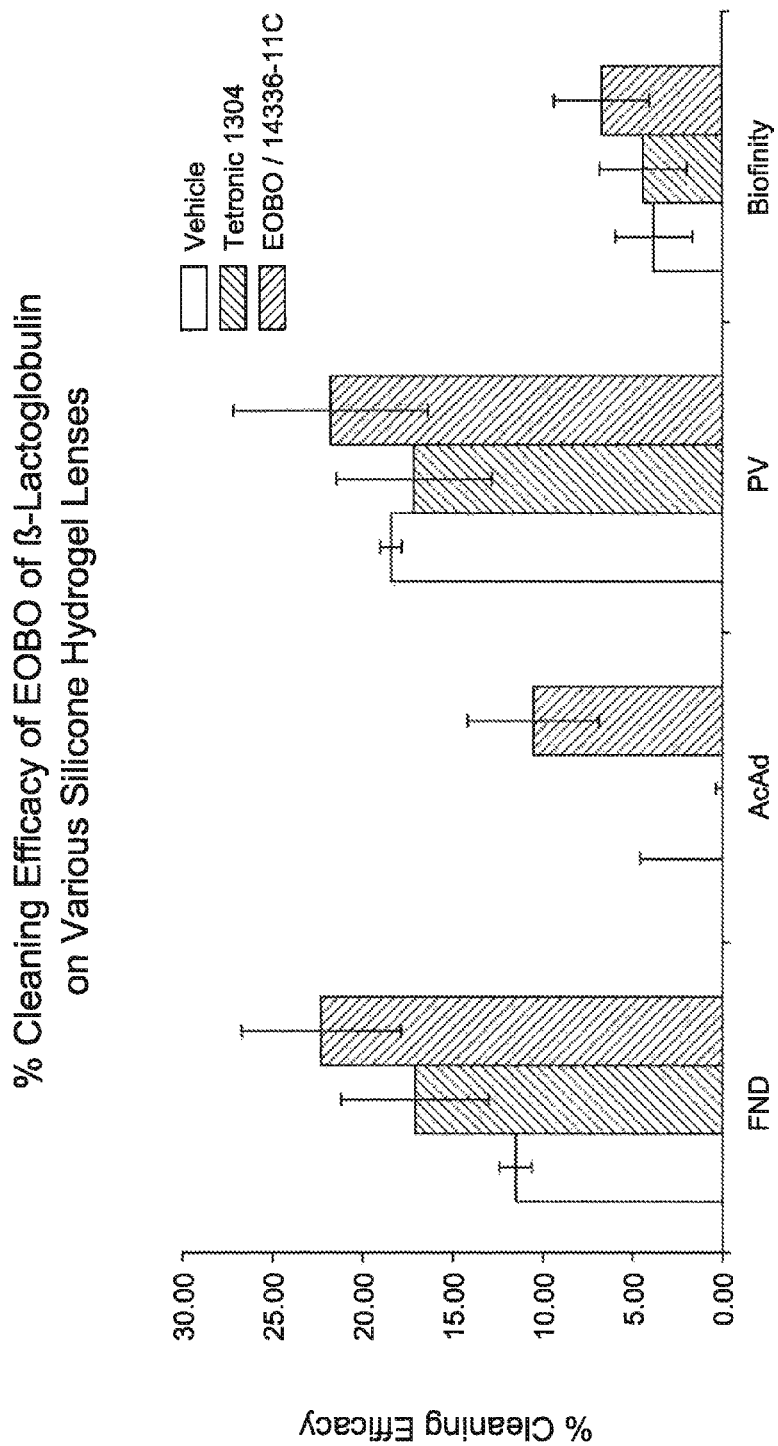

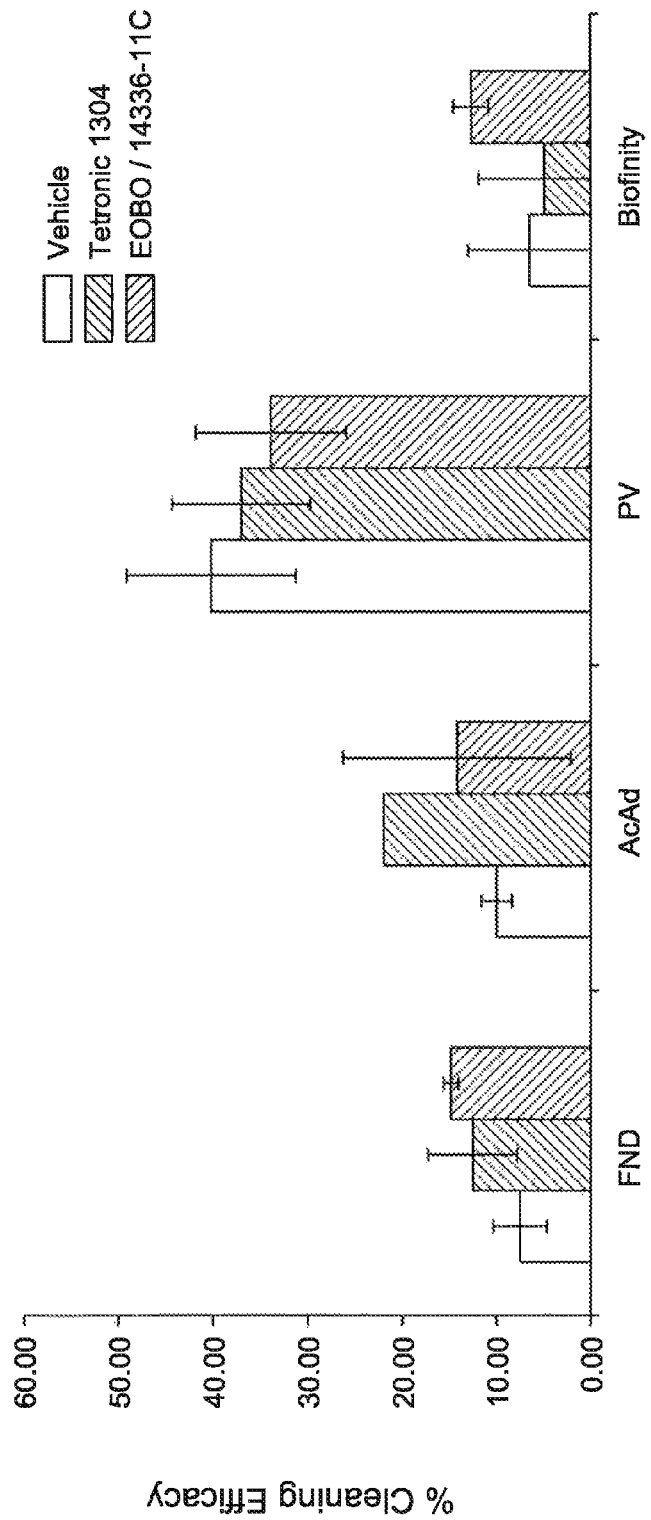

ETHYLENEOXIDE BUTYLENEOXIDE BLOCK COPOLYMER COMPOSITIONS

CROSS-REFERENCE TO RELATED APPLICATION

This application claims priority under 35 U.S.C. §119 to U.S. Provisional Patent Application No. 61/223,599, filed Jul. 7, 2009, the entire contents of which are incorporated herein by reference.

TECHNICAL FIELD OF THE INVENTION

The present invention relates generally to ethyleneoxide butyleneoxide block copolymer compositions and specifically to ethyleneoxide butyleneoxide block copolymer compositions comprising a galactomannan such as guar or a guar derivative.

BACKGROUND OF THE INVENTION

The use of polymeric ingredients in compositions, particularly topically administrable ophthalmic compositions, is well known. Polymeric ingredients are typically used in suspension compositions as physical stability aids, helping to keep the insoluble ingredients suspended or easily redispersible. Polymers also impart desirable viscoelastic and rheological characteristics to compositions of which they are a part.

Many polymers have been used in topically administrable ophthalmic compositions. Included among these are cellulosic polymers, such as hydroxypropyl methylcellulose, hydroxyethyl cellulose, and ethylhydroxyethyl cellulose. Also included are synthetic polymers, such as carboxyvinyl polymers and polyvinyl alcohol. Still others include polysaccharides such as xanthan gum, guar gum, and dextran.

Combinations of polymers have also been used in ophthalmic compositions. Certain combinations of polymers are known to provide synergistic effects on viscosity and, in some cases, even a phase transition from a liquid to a gel. For example, U.S. Pat. No. 4,136,173 discloses ophthalmic compositions containing a combination of xanthan gum and locust bean gum.

BRIEF SUMMARY OF THE INVENTION

The present invention is directed in certain embodiments to ophthalmic compositions comprising an ethyleneoxide butyleneoxide (EO-BO) block copolymer of the formula $(EO)_m(BO)_n$ and a galactomannan such as guar or a guar derivative. The present inventors have unexpectedly discovered that ethyleneoxide butyleneoxide block copolymers interact with galactomannans in aqueous solution. Aqueous compositions comprising EO-BO copolymers are generally Newtonian in behavior, and EO-BO copolymer contributes little to the viscosity of such composition at lower concentrations. However, the galactomannan and EO-BO compositions of the present invention have a synergistic increase in viscosity relative to compositions comprising galactomannan or EO-BO alone. The galactomannan and EO-BO compositions of the present invention have desirable viscoelastic and interfacial properties that make them well suited for ophthalmic applications, and in particular for contact lens disinfection and rewetting.

Ethyleneoxide butyleneoxide block copolymers are very hydrophobic amphiphiles in aqueous solutions. At an air-water interface these nonionic surfactants form elastic layers that can provide a cushioning effect for contact lenses when used in ophthalmic solutions. Furthermore, by modifying the hydrophobicity (changing the butyleneoxide unit) of EO-BO block copolymers in solution, advantageous changes in the elasticity of such solutions can occur.

In a preferred embodiment, the compositions of the present invention comprise a ethyleneoxide butyleneoxide block copolymer of the formula $(EO)_m(BO)_n$ where m is an integer having an average value of 10 to 1000 and n is an integer having an average value of 5 to 1000 and where the galactomannan is a guar derivative such as hydroxypropyl guar, native guar, or hydroxypropyl guar galactomannan.

Embodiments of the present invention also comprise the use of compositions comprising ethyleneoxide butyleneoxide block copolymer and a galactomannan in contact lens disinfection solutions, dry eye and artificial tear compositions. The present invention is also directed to methods of using these compositions to treat various ophthalmic disorders including dry eye, glaucoma, ocular hypertension, infection, allergy and inflammation.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2a-2e show steady state flow curves for EO-BO and HP-guar compositions.

FIGS. 3a-3e show stress sweep curves for EO-BO and HP-guar compositions of TABLE 2.

FIGS. 4a-4e show frequency sweep curves for EO-BO and HP-guar compositions of TABLE 2.

FIGS. 5a-5d show extensional rheology curves for EO-BO and HP-guar compositions of TABLE 2.

FIGS. 6a-6b are amplitude sweep and frequency sweep curves for EO-BO and EO-BO/HP-guar compositions.

FIGS. 7a and 7b are bar charts summarizing experiments examining the ability of EO-BO compositions of the present invention to prevent the uptake of a polar lipid (FITC-DHPE, FIG. 7a) and a non-polar lipid (NBD-cholesterol, FIG. 7b) by various silicon hydrogel contact lenses.

FIGS. 9a-9d demonstrate the cleaning efficacy of a EO-BO composition of the present invention compared to vehicle.

DETAILED DESCRIPTION OF THE INVENTION

Figure 1:
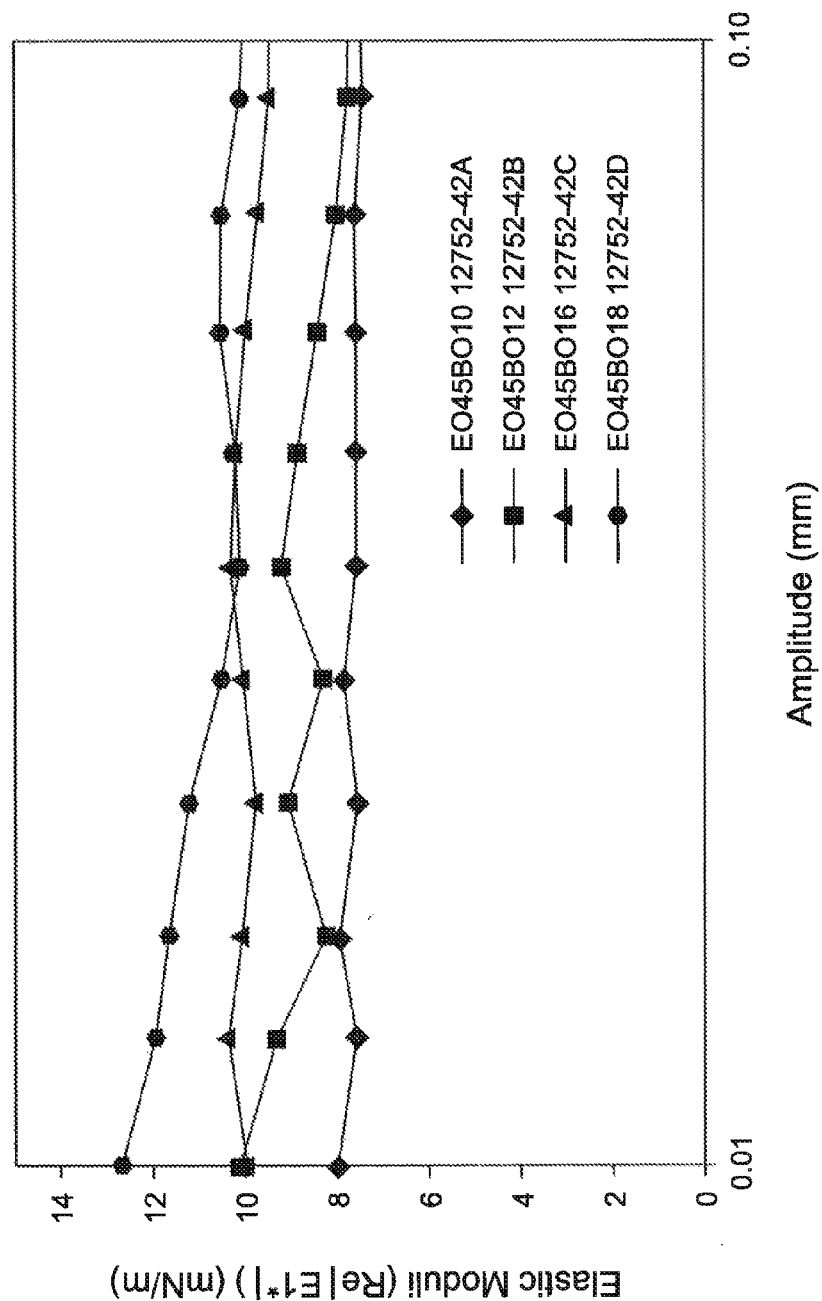
FIG. 1 shows the amplitude sweep for various EO-BO compositions.
Figure 3D:
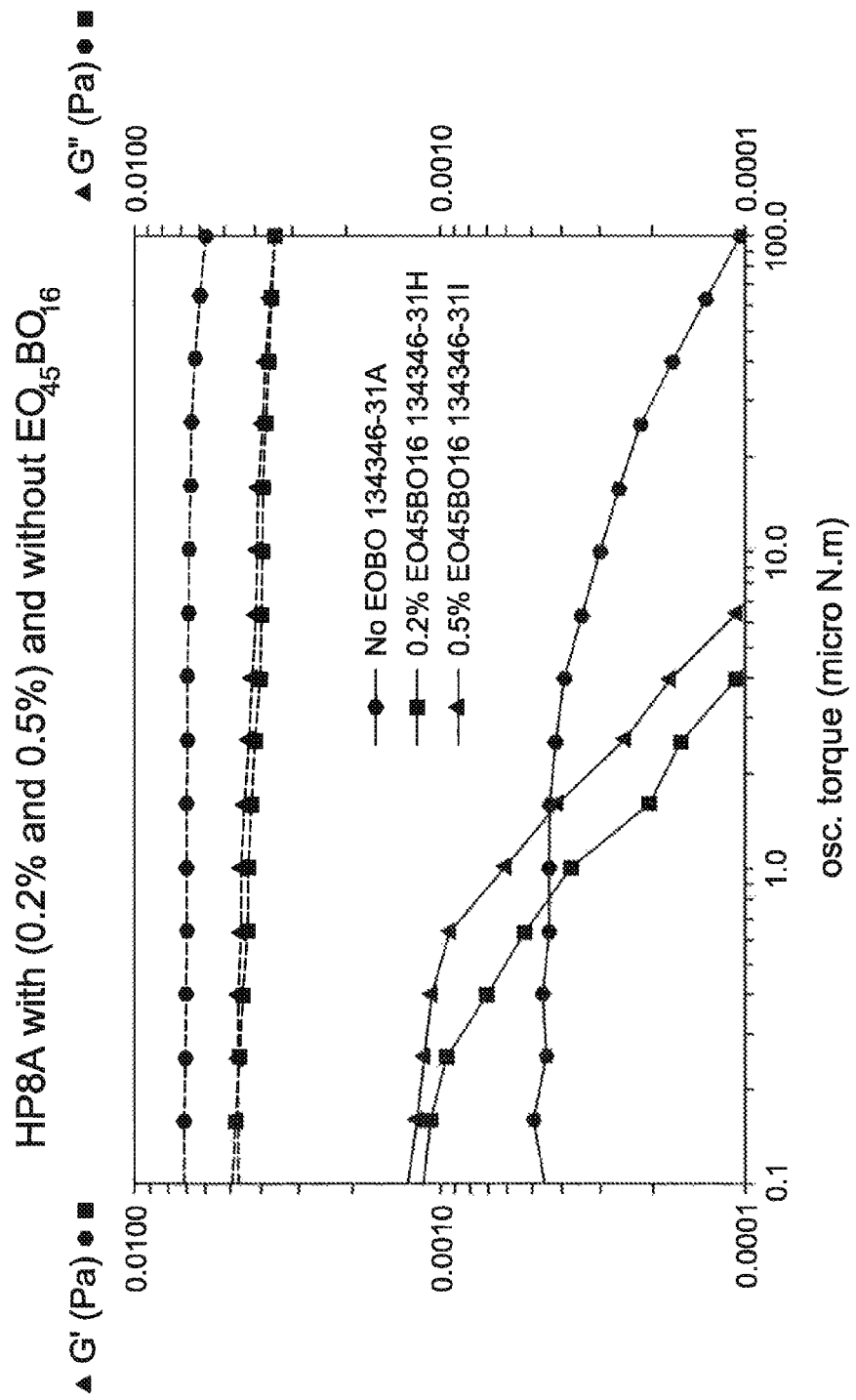

The present invention is directed in certain embodiments to ophthalmic compositions comprising an ethyleneoxide butyleneoxide (EO-BO) block copolymer and a galactomannan such as guar or a guar derivative. The ethyleneoxide butyleneoxide block copolymers of these compositions have the following general formula:

(EO)$_m$(BO)$_n$  (I)

where m is an integer having an average value of 10 to 1000 and n is an integer having an average value of 5 to 1000. The block copolymers of the present invention are those that include a poly(oxyethylene) block as the hydrophilic component and a poly(oxybutylene) block as the hydrophobic component. These may be in form of a di-block copolymer, denoted as EO-BO, a tri-block copolymer, represented as EO-BO-EO or BO-EO-BO, or other block-type configurations. Unless expressly indicated to the contrary, all references to "EO-BO block copolymers" herein include all of the foregoing forms. These copolymers may also be described in terms of the approximate or average value assigned to the respective repeating group. For example, (EO)$_{20}$(BO)$_5$, where the average value of the oxyethylene group is 20, and the average value of the oxybutylene group is 5. Compositions of the present invention generally comprise EO-BO copolymer at a concentration of 0.001 to 1.0% w/v. Preferred compositions of the present invention comprise EO-BO copolymer at a concentration of 0.01 to 0.1% w/v.

EO-BO di-block copolymers of the following general formula are particularly preferred:

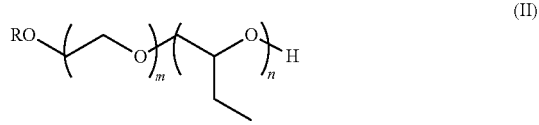
(II)

wherein R is selected from the group consisting of hydrogen, methyl, ethyl, propyl and butyl; m is an integer having an average value of 10 to 1000; and n is an integer having an average value of 5 to 1000.

Most preferred is a copolymer of formula (II) wherein R is methyl; m has an average value of 45; and n has an average value of 9-18.

The EO-BO block copolymers utilized in the present invention have a molecular weight in the range of 1,000 to about 100,000 Daltons; and more preferably in the range of 1,000 to about 15,000 Daltons.

Maintaining a proper hydrophilic-lipophilic balance (HLB) imparts certain properties to the EO-BO block co-polymer compositions of the present invention. For example, the HLB of the block co-polymers utilized in the compositions of the present invention is directly related to the solubility, surface wettability, and interfacial surface activity properties of the compositions of the present invention.

The BO portion of the block copolymer of formula (I) above is hydrophobic and is primarily responsible for the wettability properties of the compositions described herein. The EO portion of the copolymer provides the compositions with hydrophilic properties, but more importantly, it is this portion of the co-polymer that determines the aqueous solubility of the copolymers. Although it is possible to utilize solubilizing agents in the compositions of the present invention, in which case the ratio of the EO to BO segments is somewhat less critical, it is preferred to utilize copolymers that do not require solubilizing agents, as such compounds may disrupt or modify the HLB, which in turn may adversely affect the wettability properties of the compositions, cause ocular irritation, or create other concerns. Therefore, the preferred copolymers of formula (I) above are those wherein there is a predominance of EO to BO segments. That is, the variable "m" in formula (I) and formula (II) above is preferably greater than the variable "n". The EO-BO block copolymers will preferably have a ratio of EO to BO segments of from about 2:1 to about 10:1, with a ratio of about 3:1 to about 6:1 being most preferred.

The EO-BO block copolymers of the present invention may be prepared using synthetic methods known to those of skill in the art, for example, as described in Nace, V. M., J. Am. Oil Chem. Soc., Vol. 73(1):1-9, 1996; Yang et al., Macromolecules, Vol. 27:2371-2379, 1994; Yang et al., Langmuir, Vol. 11:4703, 1995; Yu et al., Langmuir, Vol. 12:3404-3412, 1996; Chaibundit et al., Langmuir, Vol. 16:9645-9652, 2000; Bedells et al., J. Chem. Soc., Faraday Trans., Vol. 89:1235-1242, 199; and Kelarakis et al., Macromolecules, Vol. 31:944-946, 1998, the entire contents of each of which are hereby incorporated in the present specification by reference. The foregoing EO-BO block copolymers may also be prepared by the application or adaptation of known methods described in U.S. Pat. No. 2,828,345 (Spriggs), and U.S. Pat. No. 2,174,761 (Schuette et al.), the entire contents of each of which are hereby incorporated into the present specification by reference. Additional synthetic procedures are taught by Ketelson et al. (U.S. patent application Ser. No. 11/953,654), the contents of which are herein incorporated by reference in its entirety.

Generally, the EO-BO block copolymers described above may be synthesized using a well defined polyethylene glycol (PEG) polymer by controlled addition of oxybutylene to the primary hydroxyl group of the PEG polymer. For example, the EO-BO di-block copolymer (EO)$_{45}$(BO)$_{10}$ may be prepared according to the following general reaction scheme:

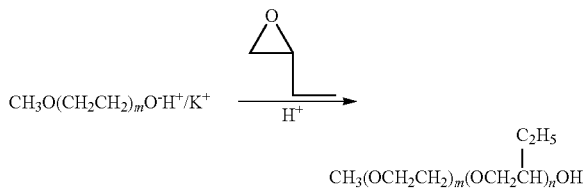

Other variations of the block chemistry structure may also be prepared, using techniques and methods readily available and well-known to those skilled in art. For example, the following reaction process may be utilized for the preparation of tri-block copolymers of the form (EO)$_m$(BO)$_n$(EO)$_m$:

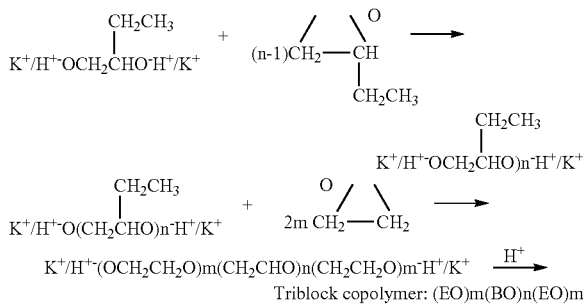

The EO-BO block copolymers of the present invention may also be functionalized with specific end groups for specific surface reactions to covalently bind the polymer to a surface or prepare a new polymer material. The EO-BO block copolymers that may be utilized in the present invention are not limited relative to structure or molecular weight, so long as the block copolymers are soluble in aqueous solutions and are non-toxic to ophthalmic tissue at concentrations on the order of those described herein.

As used herein, the term "galactomannan" refers to polysaccharides derived from the above natural gums or similar natural or synthetic gums containing mannose or galactose moieties, or both groups, as the main structural components. Several types of galactomannans that may be used in the present invention are typically derived from guar gum, locust bean gum and tara gum. The galactomannans of the present invention are obtainable from various commercial sources and via synthetic procedures known to those of skill in the art. In preferred embodiments, the galactomannan is hydroxypropyl guar (HP-8A or HP-guar) obtained from Rhodia, Inc. Other galactomannan include, but are not limited to, native guar and hydroxypropyl guar galactomannan produced according to the processes of co-pending U.S. Patent Application Ser. Nos. 61/220,859 filed Jun. 26, 2009, and 61/150,215 filed Feb. 5, 2009, the contents of which are herein incorporated by reference in their entirety. Compositions of the present invention generally comprise galactomannan at a concentration of 0.01 to 2.0% w/v. Preferred compositions of the present invention comprise galactomannan at a concentration of 0.05 to 0.25% w/v.

In addition to EO-BO block copolymer and galactomannan, the compositions of the present invention optionally comprise one or more additional components. Such components include, but are not limited to, tonicity agents, preservatives, chelating agents, buffering agents, surfactants, cosolvents, and antioxidants. Other components used in certain embodiments are solubilizing agents, stabilizing agents, comfort-enhancing agents, polymers, emollients, pH-adjusting agents and/or lubricants. Components that may be used in certain compositions of the present invention including water, mixtures of water and water-miscible solvents, such as C1-C7-alkanols, vegetable oils or mineral oils comprising from 0.5 to 5% non-toxic water-soluble polymers, natural, products, such as alginates, pectins, tragacanth, karaya gum, xanthan gum, carrageenin, agar and acacia, starch derivatives, such as starch acetate and hydroxypropyl, starch, and also other synthetic products, such as polyvinyl alcohol, polyvinylpyrrolidone, polyvinyl methyl ether, polyethylene oxide, preferably cross-linked polyacrylic acid, and mixtures of those products.

In addition to EO-BO block copolymer and galactomannan, the compositions of the present invention may comprise compounds having antimicrobial or preservative properties. Suitable antimicrobial agents include, but are not limited to those generally used in contact lens care solutions or in other ophthalmic solutions such as polyquaternium-1, which is a polymeric quaternary ammonium compound; myristamidopropyl dimethylamine ("MAPDA"), which is a N,N-dialkyl, N'-alkyl, ethylene diamine; guanidine derivatives such as polyhexamethylene biguanide ("PHMB") or polyaminopropyl biguanide (PAPB); perborates such as sodium perborate and peroxides such as hydrogen peroxide. The additional antimicrobial agents that may be utilized in the present invention also include the aminobiguanides described in U.S. Pat. No. 6,664,294, the entire contents of which are hereby incorporated in the present specification by reference. The preferred additional antimicrobial agents are polyquaternium-1, MAPDA and the amino biguanide identified in U.S. Pat. No. 6,664,294 as "Compound Number 1".

Suitable antioxidants include, but are not limited to, sulfites, ascorbates, butylated hydroxyanisole (BHA) and butylated hydroxytoluene (BHT).

In addition to EO-BO block copolymer and galactomannan, the compositions of the present invention may comprise one or more surfactants. Surfactants utilized in the compositions of the present invention can be cationic, anionic, nonionic or amphoteric. Preferred surfactants are neutral or nonionic surfactants which may present in amounts up to 5 w/v %. Surfactants that may be used with certain embodiments of the present invention include, but are not limited to, polyethylene glycol ethers or esters of fatty acids, polyoxyethylene-polyoxypropylene block copolymers of ethylene diamine (e.g., poloxamines such as Tetronic 1304 or 1107), polyoxypropylene-polyoxyethylene glycol nonionic block copolymers (e.g., poloxamers, such as Pluronic F-127), and p-isooctylpolyethylen phenol formaldehyde polymers (e.g., Tyloxapol).

In certain embodiments of the present invention, suitable cosolvents include glycerin, propylene glycol and polyethylene glycol.

Buffering agents which may be incorporated into compositions of the present invention include, but are not limited to, alkaline metal salts, such as potassium or sodium carbonates, acetates, borates, phosphates and citrates, and weak acids, such as acetic acids and boric acids. The preferred buffering agents are alkaline metal borates, such as sodium or potassium borates. Other pH-adjusting agents, such as inorganic acids and bases, may also be utilized. For example, hydrochloric acid or sodium hydroxide may be employed in concentrations suitable for ophthalmic compositions. The above-described buffering agents are generally present in amounts from about 0.1 to about 2.5 w/v %, preferably from about 0.5 to about 1.5% w/v %.

The compositions of the present invention are preferably isotonic, or slightly hypotonic, and generally have an osmolality in the range of 210-320 mOsm/kg, and preferably have an osmolality in the range of 235-300 mOsm/kg. This may require a tonicity agent to bring the osmolality of the composition to the desired level. Tonicity-adjusting agents include, but are not limited to, sodium chloride, glycerin, sorbitol, or mannitol.

In contact lens disinfection applications, disinfectants that may be used include, but are not limited to halamines, halogenated amino acids, bis-amines, and certain preservatives listed above. The amount of the disinfectant required to achieve the desired disinfection activity can be determined by persons skilled in the art. The concentration required to achieve the desired activity as a disinfectant while retaining acceptable safety and toxicity properties is referred to herein as "an effective amount". An effective amount will possess antimicrobial activity sufficient to meet generally accepted standards for activity, such as EN ISO 14729:2001 Ophthalmic optics—Contact lens care products—Microbiological requirements and test methods for products and regimens for hygienic management of contact lenses.

For ophthalmic applications of the present invention, the pH of the compositions may be in an ophthalmic acceptable range of 3.0 to 8.0. Preferred ophthalmic compositions are prepared using a buffering system that maintains the composition at a pH of about 3.0 to a pH of about 8.0.

In particular embodiments, compositions of the present invention are suitable for topical application to mammalian eyes. For example, for ophthalmic administration, the composition may be a solution, a suspension, a gel, water-in-oil and oil-in-water emulsions, or an ointment. Preferred compositions for ophthalmic administration will be aqueous solution in the form of drops. The term "aqueous" typically denotes an aqueous composition wherein the excipient is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts preservative from the composition as it is delivered, such devices being known in the art.

In certain topical ophthalmic applications, the compositions of the present invention may comprise one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Topical ophthalmic compositions of the present invention generally have a viscosity of 0.5-100 cps, preferably 0.5-50 cps, and most preferably 1-20 cps. This relatively low viscosity insures that the product is comfortable, does not cause blurring, and is easily processed during manufacturing, transfer and filling operations.

Compositions of the present invention can also be used to deliver a pharmaceutical agent to the eye. Such pharmaceutical agents include, but are not limited to anti-glaucoma agents, anti-angiogenesis agents; anti-infective agents; anti-inflammatory agents; growth factors; immunosuppressant agents; and anti-allergic agents. Anti-glaucoma agents include, but are not limited to, beta-blockers, such as betaxolol and levobetaxolol; carbonic anhydrase inhibitors, such as brinzolamide and dorzolamide; prostaglandins, such as travoprost, bimatoprost, and latanoprost; seretonergics; muscarinics; dopaminergic agonists. Anti-angiogenesis agents include, but are not limited to, anecortave acetate (RE-TAANE™, Alcon™ Laboratories, Inc. of Fort Worth, Tex.) and receptor tyrosine kinase inhibitors (RTKi). Anti-inflammatory agents include, but are not limited to, non-steroidal and steroidal anti-inflammatory agents, such as triamcinolone actinide, suprofen, diclofenac, ketorolac, nepafenac, rimexolone, and tetrahydrocortisol. Growth factors include EGF or VEGF. Anti-allergic agents include, but are not limited to olopatadine and epinastine, H1 and H4 receptor antagonists (such as those disclosed in WO 2010/030785 to Borchardt et al., herein incorporated by reference in its entirety).

EXAMPLES

The following examples are presented to further illustrate selected embodiments of the present invention.

Example 1

| Ingredient | % w/v |
| --- | --- |
| $EO_{45}BO_{14}$ | 0.2 |
| HP-Guar | 0.15 |
| Boric Acid | 0.35 |
| Sodium Borate | 0.11 |
| Sodium Chloride | 0.7 |
| Sodium Chlorite | 0.006 |
| Sodium Hydroxide/Hydrochloric Acid | pH adjust to 7.0 |
| Purified Water | QS |

Example 2

Experiments were performed to examine the rheology of EO-BO and guar compositions of the present invention. These experiments, included bulk rheology experiments including steady state flow, and frequency and stress sweeps. Extensional and interfacial rheology characterization was also performed.

Bulk rheology experiments were conducted using a controlled stress rheometer (AR 2000ex, TA Instruments, Inc.). The measurement system was a 40 mm acrylic 2° cone and plate with a sample volume of 0.58 mL. A temperature of 25'C+/−0.1° C. was maintained and a cover was placed over the measurement system to prevent evaporation of the solutions. For steady state flow (SSF) experiments, the instrument applies a controlled stress which in turn gives the result as viscosity vs. shear rate. Two dynamic tests were conducted: oscillation stress sweep and oscillation frequency sweep. The oscillation stress sweep holds the frequency of the solution constant while measuring a range of stresses. The oscillation stress sweep measures G' (elastic/storage modulus) and G" (viscous, loss modulus). From this information the linear viscoelastic region (LVR) can be determined. The LVR is a region in the stress sweep, obtained from G', where the solution holds its elasticity, G', over a range of stresses. A measure of relative elasticity, $\tan(\delta)=G"/G'$, is obtained from these experiments. The oscillation frequency sweep holds the stress constant within the LVR while measuring a range of frequencies. This measurement can determine G', G" and $\tan(\delta)$ as well. The oscillation frequency sweep shows how well a solution maintains its structure.

Interfacial rheology experiments were conducted using an optical oscillating drop generator device (OCA20, Dataphysics Instruments) equipped with a piezoelectric device and amplifier that controlled the oscillations of the drop. The drop, suspended in a temperature and humidity controlled cell at the tip of a stainless steel needle of 1.65 mm external diameter, was observed with a CCD camera (768×576 pixels) at 500 images per second. The oscillating drop generator (ODG) technique characterizes the mechanical strength of the films formed by analyzing the drop shape at a set frequency over a range of amplitudes. The amplitude changes the volume and shape of the drop and therefore the surface area.

The controlled parameters for the steady state flow experiments are as follows:
  All solutions prior to experiment had the same rheological history
  40 mm 2° Acrylic Cone.
    0.75 mL volume
    60 µm gap
  Double Concentric Cylinder
    6.8 mL volume
    500 µm gap
  Temperature was set at 25° C.
  Equilibration was set for 10 minutes after the geometry was set
  Pre-Shear of 10 s−1 for 10 sec
  Torque was set from 0.1 µNm to 100 µNm
    0.1 µNm is the lowest limit
    100 µNm and beyond is not accounted for
  5 points per decade; 5 min equilibrium at each point; triple measurements at 5% tolerance
  A 60 mm plate cover was placed over the geometry to prevent evaporation.
  Oscillation parameters:
  Stress (Torque) Sweep
    0.1 dyne·cm to 100 dyne·cm is within the raw phase for all solutions tested
    Frequency set at 0.1 Hz
  Frequency Sweep
    0.01 Hz to 10 Hz
    Torque set at 100 dyne·cm Time Sweep
  Pre shear of 100 s−1 for 10 seconds
  Frequency at 0.1 Hz and torque at 100 dyne·cm used
Extensional Parameters:
Geometry

| | |
|---|---|
| Plate Diameter | 6.00 mm |
| Sample Initial Height | 3.01 mm |
| Sample Final Height | 13.32 mm |
| Sample Volume | 80 µL |
| System Hencky Strain | 1.49 |
| Initial Aspect Ratio | 1.00 |
| Final Aspect Ratio | 4.44 |

Stretch Profile

| Type | Linear |
|---|---|
| Effective Velocity | 0.21 mm/s |
| Strike Time | 50 ms |
| Strike Distance | 10.31 mm |

Measurement Options

| Method | High Speed Digital Mode |
|---|---|
| Sample Rate | 10,000 Hz |
| Sample Duration | 1.0 s |

Note:
For sample duration longer than 1.0 sec, the sample rate was adjusted for optimal measurement.

The following is a description of the parameters and equipment used for the interfacial rheology experiment utilizing an oscillating bubble. The OCA 20 with the oscillating drop generator was used for the oscillating bubble experiment. The following are the parameters used in the experiment for each composition:

| Method | Pendant Drop Oscillating Volume |
|---|---|
| Needle | 1.65 mm |
| Bubble Equilibration Time | 3.5 Hours |
| Iteration Step | 20 (logarithmic) |
| Frequency | 0.1 s-1 |
| Amplitude | 0.003 mm-0.3 mm |
| Duration per Step | 40 sec |
| Images per Step | 1000 |
| Temperature | 25° C. |

Prior to each run the system was checked and standardized by confirming the surface tension of water at 72.5 mN/m at 25° C. in air. A quartz cuvete was filled half full with purified water and placed below the drops while out of the view of the camera. This was to prevent water loss of the drop during equilibration and throughout the experiment. Before the each oscillating bubble experiment began, the bubbles equilibrated for a time of not less than 3.5 hours.

TABLES 1 and 2 below detail compositions tested in the EO-BO interfacial rheology and EO-BO/guar rheology experiments, respectively. All compositions of TABLE 2 also comprise 1.0% boric acid, 0.35% NaCl, and 0.001% polyquaternium-1, and have a pH of 7.5.

TABLE 1

| Composition Chemical (% wt/% vol.) | 12752-42A | 12752-42B | 12752-42C | 12752-42D |
|---|---|---|---|---|
| $EO_{45}BO_{10}$ | 0.05 | — | — | — |
| $EO_{45}BO_{12}$ | — | 0.05 | — | — |
| $EO_{45}BO_{16}$ | — | — | 0.05 | — |
| $EO_{45}BO_{18}$ | — | — | — | 0.05 |
| pH | 7.5 | 7.5 | 7.5 | 7.5 |
| Purified Water (QS = 100 mL) | QS | QS | QS | QS |

TABLE 2

| Composition Chemical (% wt/% vol.) | 134346-31A | 134346-31B | 134346-31C | 134346-31D | 134346-31E | 134346-31F | 134346-31G | 134346-31H | 134346-31I | 134346-31J | 134346-31K |
|---|---|---|---|---|---|---|---|---|---|---|---|
| HP-Guar | 0.15 | 0.15 | 0.15 | 0.15 | 0.15 | 0.15 | 0.15 | 0.15 | 0.15 | 0.15 | 0.15 |
| $EO_{45}BO_9$ | — | 0.2 | 0.5 | — | — | — | — | — | — | — | — |
| $EO_{45}BO_{11}$ | — | — | — | 0.2 | 0.5 | — | — | — | — | — | — |
| $EO_{45}BO_{14}$ | — | — | — | — | — | 0.2 | 0.5 | — | — | — | — |
| $EO_{45}BO_{16}$ | — | — | — | — | — | — | — | 0.2 | 0.5 | — | — |
| $EO_{45}BO_{18}$ | — | — | — | — | — | — | — | — | — | 0.2 | 0.5 |
| Break up Times (s) | 0.131 | 0.247 | 0.323 | 0.361 | 0.342 | 0.118 | 0.146 | 0.140 | 0.180 | 0.104 | 0.138 |
| Visc. (cPs) @ 10.0 s-1 | 10.54 | 10.59 | 11.00 | 12.70 | 11.22 | 6.80 | 5.20 | 6.12 | 6.09 | 4.80 | 4.64 |

FIG. 1 shows the amplitude sweep for the EO-BO compositions of TABLE 1. The graphs demonstrate that the elastic contribution at the air-water interface for these EO-BO compositions increases as the BO unit size increases from $BO_{10}$ to $BO_{18}$.

FIGS. 2a-2e show steady state slow curves for EO-BO and HP-Guar compositions of TABLE 2. The graphs show that shear thinning is reduced as the EO-BO block copolymer concentration increases. $EO_{45}BO_{9-11}$ compositions have similar viscosity profiles compared to the composition containing only HP-guar. $EO_{45}BO_{14-18}$ compositions have shear thinning profiles which are similar that of the composition containing only HP-guar; however, their viscosities are lower than the composition containing only HP-guar.

FIGS. 3a-3e show stress sweep curves for EO-BO and HP-Guar compositions of TABLE 2. The curves demonstrate that all compositions tested are viscous (G") dominant solutions with elasticity (0', structure). $EO_{45}BO_{9-11}$ compositions have a similar structure to the composition containing only HP-guar, with similar linear viscoelastic regions. $EO_{45}BO_{14-18}$ compositions have some structure, but have linear viscoelastic regions that drop off rapidly as the shear rate increases.

FIGS. 4a-4e show frequency sweep curves for EO-BO and HP-Guar compositions of TABLE 2. $EO_{45}BO_{9-11}$ compositions have a similar structure to the composition containing only HP-guar throughout the frequency sweep. $EO_{45}BO_{14-18}$ compositions have some structure, which drops off rapidly at higher frequency.

FIGS. 5a-5d show extensional rheology curves for the EO-BO and HP-guar compositions of TABLE 2. The curves demonstrate that $EO_{45}BO_{9-11}$ compositions have longer break up times than the composition containing only HP-guar. $EO_{45}BO_{14-18}$ compositions have similar break up times compared to the composition containing only HP-guar. $EO_{45}BO_{9-11}$ compositions also have higher extensional viscosities relative to the composition containing only HP-guar. $EO_{45}BO_{14-18}$ compositions have similar extensional viscosities relative to the composition containing only HP-guar. The effect of EO-BO compositions was seen in other galactomannans such as native guar. As shown in TABLE 3 below, EO-BO increased the break up times for compositions comprising both HP-guar and native guar.

TABLE 3

| Sample | Concentration | pH | Break Up Time |
|---|---|---|---|
| A | 0.2% HP8A/0.04% EOBO | 7.5 | 0.09264 |
| B | 0.2% HP8A | 7.5 | 0.09922 |
| C | 0.2% Native Guar/0.04% EOBO | 7.5 | 0.10002 |
| D | 0.2% Native Guar/0.04% EOBO | 7.5 | 0.08642 |
| E | 0.2% Native Guar/0.2% EOBO | 7.5 | 0.09602 |
| F | 0.2% Native Guar | 7.5 | 0.09042 |
| A | 0.2% HP8A/0.04% EOBO | 8.0 | 0.21142 |
| B | 0.2% HP8A | 8.0 | 0.27863 |
| C | 0.2% Native Guar/0.04% EOBO | 8.0 | 0.32863 |
| D | 0.2% Native Guar/0.04% EOBO | 8.0 | 1.39927 |
| E | 0.2% Native Guar/0.2% EOBO | 8.0 | 2.12335 |
| F | 0.2% Native Guar | 8.0 | 1.67517 |

FIGS. 6a-6b show amplitude sweep and frequency sweep curves for EO-BO and HP-guar compositions of TABLE 2. For the amplitude and frequency sweeps, both $EO_{45}BO_{11}$ and $EO_{45}BO_{16}$ compositions are elastic dominant at the air-water interface. However, $EO_{45}BO_{16}$ has more structure relative to $EO_{45}BO_{11}$. EO-BO dominates the structure at the air-water interface at the tested concentrations compared to guar.

The above rheology characterizations demonstrate the compositions of the present invention are well suited for ophthalmic applications and particularly topical ophthalmic applications. In particular, EO-BO and guar compositions may provide additional tear film stability when used in dry eye compositions.

Example 3

Compositions of the present invention were tested for their ability to (i) prevent deposition of lipids and proteins on silicon hydrogel lenses and (ii) to clean lenses of lipid and protein deposits. TABLE 4 is a summary of the lenses tested, and TABLES 5 and 6 list compositions that were tested.

TABLE 4

| Brand Name | Manufacturer |
|---|---|
| Acuvue ® Advance ™ | Vistakon ® |
| PureVision ™ | Bausch and Lomb ® |
| Focus Night&Day ™ | Ciba Vision ® |
| Biofinity ® | Cooper Vision |

TABLE 5

| Composition Chemical (% wt/vol.) | 14336-11A | 14336-11B | 14336-11C |
|---|---|---|---|
| Polyquaternium-1 | 0.001 | 0.001 | 0.001 |
| N[3-dimethylamino propyl] tetra decanamide | 0.0006 | 0.0006 | 0.0006 |
| $EO_{45}BO_{11}$ | — | — | 0.04 |
| Tetronic 1304 | — | 0.04 | 0.04 |
| Sorbitol | 1.2 | 1.2 | 1.2 |
| Boric Acid | 0.6 | 0.6 | 0.6 |
| Sodium Citrate | 0.65 | 0.65 | 0.65 |
| Sodium Chloride | 0.1 | 0.1 | 0.1 |
| EDTA | 0.05 | 0.05 | 0.05 |
| 2-amino-2-methyl-1-propanol | 0.42 | 0.42 | 0.42 |
| Purified Water | QS | QS | QS |
| pH | 7.8 | 7.8 | 7.8 |

TABLE 6

| Composition Chemical (% wt/% vol) | 13990-23A | 13990-23B | 13990-23C | 13990-23D |
|---|---|---|---|---|
| Polyquaternium-1 | 0.001 | 0.001 | 0.001 | 0.001 |
| N[3-dimethylamino propyl] tetra decanamide | 0.0007 | 0.0008 | 0.0007 | 0.0008 |
| $EO_{45}BO_9$ | 0.05 | 0.05 | — | — |
| $EO_{45}BO_{11}$ | — | — | 0.05 | 0.05 |
| Tetronic 1304 | 0.05 | 0.05 | 0.05 | 0.05 |
| Sorbitol | 1.2 | 1.2 | 1.2 | 1.2 |
| Boric Acid | 0.6 | 0.6 | 0.6 | 0.6 |
| Sodium Citrate | 0.65 | 0.65 | 0.65 | 0.65 |
| Sodium Chloride | 0.1 | 0.1 | 0.1 | 0.1 |
| EDTA | 0.05 | 0.05 | 0.05 | 0.05 |
| 2-amino-2-methyl-1-propanol | 0.42 | 0.42 | 0.42 | 0.42 |
| Purified Water | QS | QS | QS | QS |
| pH | 7.8 | 7.8 | 7.8 | 7.8 |

The bar charts of FIGS. 7a and 7b summarize experiments examining the ability of EO-BO compositions of the present invention to prevent the uptake of a polar lipid (FITC-DHPE, FIG. 7a) and a non-polar lipid (NBD-cholesterol, FIG. 7b) by the silicon hydrogel lenses of TABLE 4. The results illustrate that the compositions (Lot 13990-23A and 23C, TABLE 6) are particularly effective at preventing the uptake of the non-polar lipid by all lenses tested.

Figure 8:
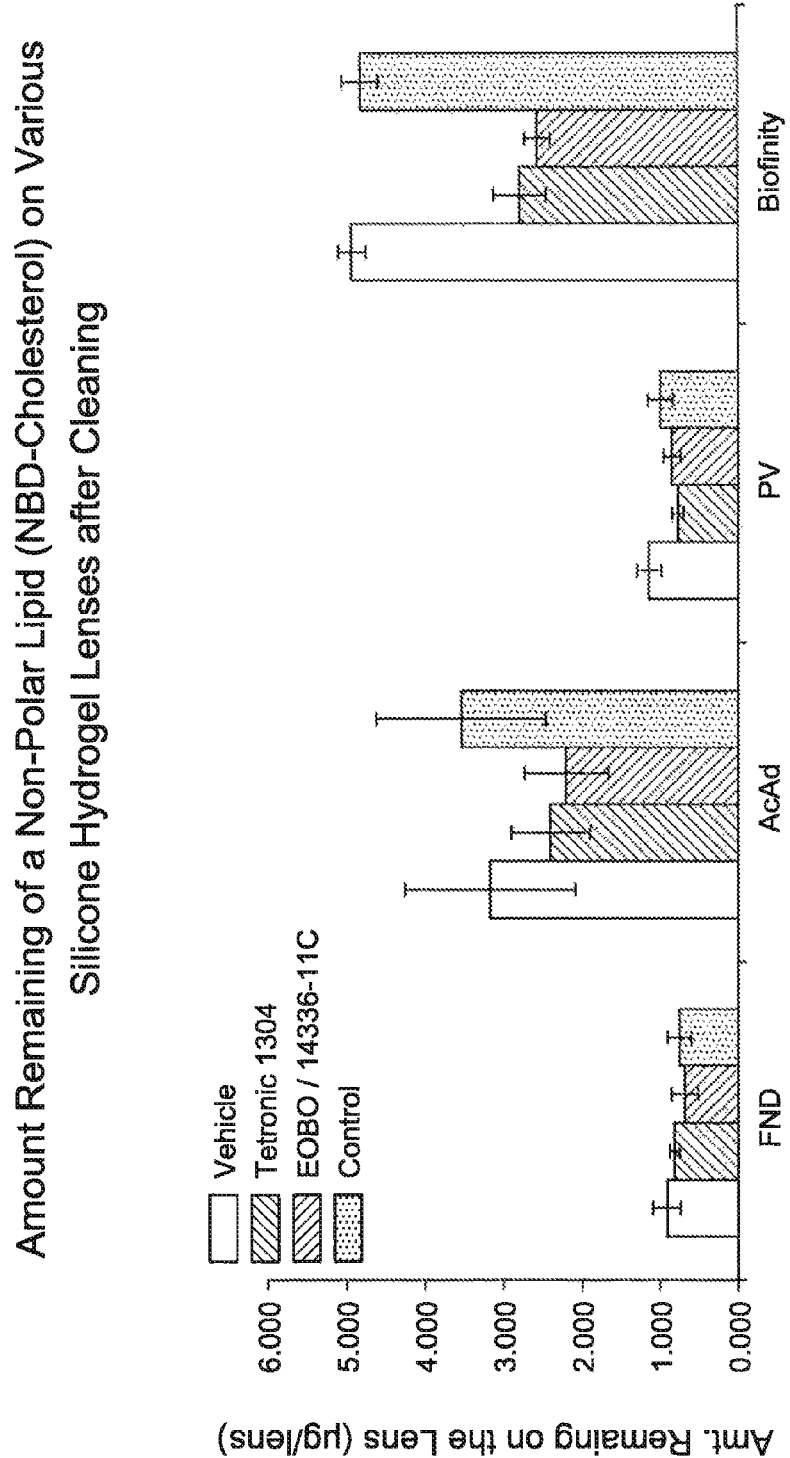
FIG. 8 is a bar chart showing the amount remaining of a non-polar lipid (NBD-cholesterol) on various silicon hydrogel lenses after treatment with compositions containing EO-BO and HP-guar.

FIG. 8 shows a bar chart showing the amount remaining of a non-polar lipid (NBD-cholesterol) on the lenses of TABLE 4 after cleaning with various test compositions. The chart illustrates that a composition of the present invention (14336-11C, TABLE 5) tested removes non-polar lipid deposits from silicone hydrogel contact lenses better than the other tested compositions in 3 out of 4 lenses.

FIGS. 9a-9d demonstrate that a composition of the present invention (14336-11C, TABLE 5) is effective at cleaning various proteins (lysozyme, lactoferrin, beta-lactoglobulin) from the tested lenses of TABLE 4.

In summary, the results of the experiments demonstrate that compositions of the present invention are effective lens cleaners and can prevent the uptake of non-polar lipids. The compositions are also particularly effective at removing non-polar lipid deposits from lenses.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A sterile, aqueous ophthalmic composition comprising an ethyleneoxide butyleneoxide (EO-BO) block copolymer of the formula $(EO)_m(BO)_n$ and a galactomannan, and wherein m has an average value of 45 and n has an average value of 9 to 18.

2. A composition according to claim 1 wherein m has an average value of 45 and n has an average value of 9 to 11.

3. A composition according to claim 1 wherein said galactomannan is guar.

4. A composition according to claim 3 wherein said guar or guar derivative is selected from the group consisting of: native guar, hydroxypropyl guar, and hydroxypropyl guar galactomannan.

5. A composition according to claim 1 wherein said EO-BO block copolymer is present at a concentration of 0.001 to 1.0% w/v.

6. A composition according to claim 1 wherein said EO-BO block copolymer is present at a concentration of 0.01 to 0.1% w/v.

7. A composition according to claim 1 wherein said galactomannan is present at a concentration of 0.01 to 2.0% w/v.

8. A composition according to claim 1 wherein said galactomannan is present at a concentration of 0.05 to 0.25% w/v.

9. A method of delivering a pharmaceutical agent to the eye which comprises topically administering to the eye a composition comprising one or more pharmaceutically active agent(s), an ethyleneoxide butyleneoxide block copolymer of the formula $(EO)_m(BO)_n$ and a galactomannan, and wherein m has an average value of 45 and n has an average value of 9 to 18.

10. A composition according to claim 9, wherein the pharmaceutically active agent(s) is/are selected from the group consisting of: anti-glaucoma agents, anti-angiogenesis agents; anti-infective agents; anti-inflammatory agents; growth factors; immunosuppressant agents; and anti-allergic agents.

* * * * *